United States Patent
Tomizawa et al.

(10) Patent No.: US 10,526,654 B2
(45) Date of Patent: Jan. 7, 2020

(54) SIMPLE DETECTION METHOD FOR RNA MODIFICATION, AND METHOD FOR DETECTING TYPE-II DIABETES USING SAID DETECTION METHOD

(71) Applicant: National University Corporation Kumamoto University, Kumamoto (JP)

(72) Inventors: Kazuhito Tomizawa, Kumamoto (JP); Fanyan Wei, Kumamoto (JP); Takeo Suzuki, Tokyo (JP); Tsutomu Suzuki, Tokyo (JP)

(73) Assignee: NATIONAL UNIVERSITY CORPORATION KUMAMOTO UNIVERSITY, Kumamoto (JP)

( * ) Notice: Subject to any disclaimer, the term of this patent is extended or adjusted under 35 U.S.C. 154(b) by 917 days.

(21) Appl. No.: 14/772,969

(22) PCT Filed: Mar. 6, 2014

(86) PCT No.: PCT/JP2014/055758
§ 371 (c)(1),
(2) Date: Nov. 19, 2015

(87) PCT Pub. No.: WO2014/136870
PCT Pub. Date: Sep. 12, 2014

(65) Prior Publication Data
US 2016/0060698 A1 Mar. 3, 2016

(30) Foreign Application Priority Data

Mar. 8, 2013 (JP) ................................. 2013-047278
Jul. 19, 2013 (JP) ................................. 2013-150133

(51) Int. Cl.
*C12Q 1/68* (2018.01)
*C12Q 1/6883* (2018.01)
*G16B 20/00* (2019.01)

(52) U.S. Cl.
CPC .......... *C12Q 1/6883* (2013.01); *G16B 20/00* (2019.02); *C12Q 2600/112* (2013.01);
(Continued)

(58) Field of Classification Search
None
See application file for complete search history.

(56) References Cited

FOREIGN PATENT DOCUMENTS

| CN | 102356160 | 2/2012 |
| JP | 2007-509613 A | 4/2007 |

(Continued)

OTHER PUBLICATIONS

Echevarria et al. Simultaneous detection and identification of human parainfluenza viruses 1, 2, and 3 from clinical samples by multiplex PCR. Journal of Clinical Microbiology 36(5):1388-1391. (Year: 1991).*

(Continued)

*Primary Examiner* — Samuel C Woolwine
(74) *Attorney, Agent, or Firm* — Hunton Andrews Kurth LLP

(57) ABSTRACT

An object of the present invention is to provide a method for detecting a modification present in RNA using a small amount of RNA sample. Another object of the present invention is to provide a method for detecting a modification present in tRNA, for example, thiomethylation. Still another object of the present invention is to provide a method for detecting the thiomethylation of tRNA, thereby diagnosing human type 2 diabetes or the risk thereof. The present invention is characterized in that, with respect to a modification present in RNA in an RNA sample, cDNA is produced by reverse transcription of RNA using a first primer, and the resulting amount of cDNA is compared with the amount of cDNA produced by reverse transcription of RNA using a (Continued)

second primer, thereby detecting a modification (e.g., thiomethylation) present in RNA.

20 Claims, 8 Drawing Sheets

Specification includes a Sequence Listing.

(52) U.S. Cl.
CPC .. *C12Q 2600/118* (2013.01); *C12Q 2600/154* (2013.01); *C12Q 2600/156* (2013.01)

(56) References Cited

FOREIGN PATENT DOCUMENTS

| | | |
|---|---|---|
| JP | 2007-295855 A | 11/2007 |
| WO | 2005/040396 | 5/2005 |
| WO | 2007/018169 A1 | 2/2007 |
| WO | 2008/109945 A1 | 9/2008 |
| WO | 2008/149855 A1 | 12/2008 |
| WO | 2010/084154 | 7/2010 |

OTHER PUBLICATIONS

Mishima et al. Site-specific crosslinking of 4-thiouridine-modified human tRNALys3 to reverse transcriptase from human immunodeficiency virus type I. The EMBO Journal 14(11): 2679-2687. (Year: 1995).*

Chambers et al. "Parainfluenza Viruses". Encyclopedia of Life Sciences. John Wiley & Sons, Ltd. www.els.net. DOI: 10.1002/9780470015902.a0001078.pub3 (8 pages) (Year: 2011).*

GenBank X55803 [online] Apr. 18, 2005 [retrieved on Oct. 8, 2018] retrieved from https://www.ncbi.nlm.nih.gov/nuccore/X55803.1 (Year: 2005).*

Kirino et al., "Specific Correlation Between the Wobble Modification Deficiency in Mutant tRNAs and the Clinical Features of a Human Mitochondrial Disease", PNAS, 102(20), May 17, 2005, pp. 7127-7132.

Vendeix et al., "Human tRNA(Lys3)(UUU) Is Pre-Structured by Natural Modifications for Cognate and Wobble Codon Binding through Keto-Enol Tautomerism", Journal of Molecular Biology, (2012) 416, pp. 467-485.

Xie et al., "Simple and Rapid Detection of 2-Methylthio Modification in tRNA for Diagnostic Application of Type 2 Diabetes", Dai 90 Kai The Physiological Society of JapanTaikai, May 29, 2013, S248, pp. 3PK-060.

Arragain et al., "Identification of Eukaryotic and Prokaryotic Methylthiotransferase for Biosynthesis of 2-Methylthio-N6-Threonylcarbamoyladenosine in tRNA" The Journal of Biological Chemistry, 285(37), Sep. 10, 2010, pp. 28425-28433.

Wei et al., "Functional Loss and Cdkal1, a Novel tRNA Modification Enzyme, Causes the Development of Type 2 Diabetes", Endocrine Journal, 58(10), 2011, pp. 819-825.

Wei et al., "Deficit of tRNA Lys Modification by Cdkal1 Causes the Development of Type 2 Diabetes in Mice" The Journal of Clinical Investigation, 121(9), Sep. 2011, pp. 3598-3608.

Reiter et al., "The CDK5 Repressor CDK5RAP1 is a Methylthiotransferase Acting on Nuclear and Mitochondrial RNA", Nucleic Acids Research, Mar. 15, 2012, 40(13), pp. 6235-6240.

Suzuki et al., "Mass Spectrometric Identification and Characterization of RNA-Modifying Enzymes", Methods of Enzymology, (2007) 425, pp. 211-229.

International Search Report issued in International Patent Application No. PCT/JP2014/055758, dated Jun. 10, 2014.

International Preliminary Report on Patentability for PCT/JP2014/055758, issuance of report dated Sep. 8, 2015.

Taira, Hikaru, et al., "In Vitro Selection of tRNAs for Efficient Four-Base Decoding to Incorporate Non-Natural Amino Acids Into Proteins in an *Escherichia coli* Cell-Free Translation System," Nucleic Acids Research, Mar. 20, 2006, vol. 34, No. 5, pp. 1653-1662.

Warner, Gregory J., "Identification and Sequencing of Two Isopentenyladenosine-Modified Transfer RNAs from Chinese Hamster Ovary Cells," Nucleic Acids Research, Dec. 1, 1998, vol. 26, No. 23, pp. 5533-5535.

Xie, Peiyu, et al., "Quantitative PCR Measurement of tRNA 2-Methylthio Modification for Assessing Type 2 Diabetes Risk," Clinical Chemistry, Nov. 2013, vol. 59, No. 11, pp. 1604-1612.

Extended European Search Report issued in European Patent Application 14 75 9799, dated Mar. 7, 2017.

Motorin, Yuri, et al., "Identification of Modified Residues in RNAs by Reverse Transcription-Based Methods," Methods in Enzymology, 2007, vol. 425, pp. 21-53.

Yano et al., "Genome-wide exploring A-to-I RNA editing sites in human transcriptome", Clinical Testing, 55(9), Sep. 15, 2011, 858-864.

Hao, Rui et al., "Human Mitochondrial tRNA Modification and Inherited Encephalomyopathies," Progess in Biochemistry and Biophysics, vol. 33, No. 5, pp. 418-422, 2006.

\* cited by examiner a  tRNA^Lys(UUU) from WT mice
   ms² modification (+)

b  tRNA^Lys(UUU) from Cdkal1 KO mice
   ms² modification (−)

a  Total RNAs in WT mice
   ms² modification (+)

b  Total RNAs in Cdkal1 KO mice
   ms² modification (−)

n=7, *p=0.029 vs. non-risk SNPs by Student's t-test

SEQUENCE LISTING

<160> NUMBER OF SEQ ID NOS: 36

<210> SEQ ID NO 1
<211> LENGTH: 73
<212> TYPE: DNA
<213> ORGANISM: Artificial Sequence
<220> FEATURE:
<223> OTHER INFORMATION: human and mouse tRNA(Lys)
<220> FEATURE:
<221> NAME/KEY: ms2t6a
<222> LOCATION: (37)..(37)

<400> SEQUENCE: 1

```
gcccggatag ctcagtcggt agagcatcag acttttaatc tgagggtcca gggttcaagt      60
ccctgttcgg gcg                                                         73
```

<210> SEQ ID NO 2
<211> LENGTH: 20
<212> TYPE: DNA
<213> ORGANISM: Artificial Sequence
<220> FEATURE:
<223> OTHER INFORMATION: foward primer

<400> SEQUENCE: 2

```
gtcggtagag catcagactt                                                  20
```

<210> SEQ ID NO 3
<211> LENGTH: 20
<212> TYPE: DNA
<213> ORGANISM: Artificial Sequence
<220> FEATURE:
<223> OTHER INFORMATION: reverse primer r1

<400> SEQUENCE: 3

```
cctggaccct cagattaaaa                                                  20
```

<210> SEQ ID NO 4
<211> LENGTH: 20
<212> TYPE: DNA
<213> ORGANISM: Artificial Sequence
<220> FEATURE:
<223> OTHER INFORMATION: reverse primer r2

<400> SEQUENCE: 4

```
gaacagggac ttgaaccctg                                                  20
```

<210> SEQ ID NO 5
<211> LENGTH: 67
<212> TYPE: DNA
<213> ORGANISM: Artificial Sequence
<220> FEATURE:
<223> OTHER INFORMATION: mouse mitochondrial tRNA(Trp)
<220> FEATURE:
<221> NAME/KEY: ms2t6a
<222> LOCATION: (35)..(35)

<400> SEQUENCE: 5

```
agaagtttag gatatactag tccgcgagcc ttcaaagccc taagaaaaca cacaagttta      60
acttctg                                                                67
```

<210> SEQ ID NO 6
<211> LENGTH: 20
<212> TYPE: DNA
<213> ORGANISM: Artificial Sequence
<220> FEATURE:
<223> OTHER INFORMATION: forward primer

<400> SEQUENCE: 6

```
ggatatacta gtccgcgagc                                                  20
```

<210> SEQ ID NO 7
<211> LENGTH: 20
<212> TYPE: DNA
<213> ORGANISM: Artificial Sequence
<220> FEATURE:
<223> OTHER INFORMATION: reverse primer r1

<400> SEQUENCE: 7
gtgttttctt agggctttga                                              20

<210> SEQ ID NO 8
<211> LENGTH: 23
<212> TYPE: DNA
<213> ORGANISM: Artificial Sequence
<220> FEATURE:
<223> OTHER INFORMATION: reverse primer r2

<400> SEQUENCE: 8
gttaaacttg tgtgttttct tag                                          23

<210> SEQ ID NO 9
<211> LENGTH: 68
<212> TYPE: DNA
<213> ORGANISM: Artificial Sequence
<220> FEATURE:
<223> OTHER INFORMATION: mouse mitochondrial tRNA(Phe)
<220> FEATURE:
<221> NAME/KEY: ms2t6a
<222> LOCATION: (36)..(36)

<400> SEQUENCE: 9
gttaatgtag cttaataaca aagcaaagca ctgaaaatgc ttagatggat aattgtatcc   60
cataaaca                                                            68

<210> SEQ ID NO 10
<211> LENGTH: 21
<212> TYPE: DNA
<213> ORGANISM: Artificial Sequence
<220> FEATURE:
<223> OTHER INFORMATION: forward primer

<400> SEQUENCE: 10
gcttaataac aaagcaaagc a                                            21

<210> SEQ ID NO 11
<211> LENGTH: 20
<212> TYPE: DNA
<213> ORGANISM: Artificial Sequence
<220> FEATURE:
<223> OTHER INFORMATION: reverse primer r1

<400> SEQUENCE: 11
tatccatcta agcattttca                                              20

<210> SEQ ID NO 12
<211> LENGTH: 20
<212> TYPE: DNA
<213> ORGANISM: Artificial Sequence
<220> FEATURE:
<223> OTHER INFORMATION: rreverse primer r2

<400> SEQUENCE: 12
tgggatacaa ttatccatct                                              20

<210> SEQ ID NO 13
<211> LENGTH: 69
<212> TYPE: DNA
<213> ORGANISM: Artificial Sequence
<220> FEATURE:
<223> OTHER INFORMATION: mouse mitochondrial tRNA(Ser)
<220> FEATURE:
<221> NAME/KEY: ms2t6a

```
<222> LOCATION: (34)..(34)

<400> SEQUENCE: 13
gagaaagaca tataggatat gagattggct tgaaaccaat tttaggggt tcgattcctt    60 cctttctta                                                          69

<210> SEQ ID NO 14
<211> LENGTH: 21
<212> TYPE: DNA
<213> ORGANISM: Artificial Sequence
<220> FEATURE:
<223> OTHER INFORMATION: forward primer

<400> SEQUENCE: 14
catataggat atgagattgg c                                            21

<210> SEQ ID NO 15
<211> LENGTH: 21
<212> TYPE: DNA
<213> ORGANISM: Artificial Sequence
<220> FEATURE:
<223> OTHER INFORMATION: reverse primer r1

<400> SEQUENCE: 15
aaccccctaa aattggtttc a                                            21

<210> SEQ ID NO 16
<211> LENGTH: 20
<212> TYPE: DNA
<213> ORGANISM: Artificial Sequence
<220> FEATURE:
<223> OTHER INFORMATION: reverse primer r2

<400> SEQUENCE: 16
gaaggaatcg aacccccta                                               20

<210> SEQ ID NO 17
<211> LENGTH: 75
<212> TYPE: DNA
<213> ORGANISM: Artificial Sequence
<220> FEATURE:
<223> OTHER INFORMATION: mouse mitochondrial tRNA(Leu)
<220> FEATURE:
<221> NAME/KEY: ms2t6a
<222> LOCATION: (39)..(39)

<400> SEQUENCE: 17
attagggtgg cagagccagg aaattgcgta agacttaaaa ccttgttccc agaggttcaa    60
atcctctccc taata                                                   75

<210> SEQ ID NO 18
<211> LENGTH: 20
<212> TYPE: DNA
<213> ORGANISM: Artificial Sequence
<220> FEATURE:
<223> OTHER INFORMATION: forward primer

<400> SEQUENCE: 18
agccaggaaa ttgcgtaaga                                              20

<210> SEQ ID NO 19
<211> LENGTH: 20
<212> TYPE: DNA
<213> ORGANISM: Artificial Sequence
<220> FEATURE:
```

<223> OTHER INFORMATION: reverse primer r1

<400> SEQUENCE: 19
cctctgggaa caaggtttta                                           20

<210> SEQ ID NO 20
<211> LENGTH: 20
<212> TYPE: DNA
<213> ORGANISM: Artificial Sequence
<220> FEATURE:
<223> OTHER INFORMATION: reverse primer r2

<400> SEQUENCE: 20
aggatttgaa cctctgggaa                                           20

<210> SEQ ID NO 21
<211> LENGTH: 68
<212> TYPE: DNA
<213> ORGANISM: Artificial Sequence
<220> FEATURE:
<223> OTHER INFORMATION: human mitochondrial rRNA(Trp)
<220> FEATURE:
<221> NAME/KEY: ms2t6a
<222> LOCATION: (36)..(36)

<400> SEQUENCE: 21
agaaatttag gttaaataca gaccaagagc cttcaaagcc ctcagtaagt tgcaatactt    60
aatttctg                                                         68

<210> SEQ ID NO 22
<211> LENGTH: 21
<212> TYPE: DNA
<213> ORGANISM: Artificial Sequence
<220> FEATURE:
<223> OTHER INFORMATION: forward primer

<400> SEQUENCE: 22
ggttaaatac agaccaagag c                                         21

<210> SEQ ID NO 23
<211> LENGTH: 21
<212> TYPE: DNA
<213> ORGANISM: Artificial Sequence
<220> FEATURE:
<223> OTHER INFORMATION: reverse primer r1

<400> SEQUENCE: 23
caacttactg agggctttga a                                         21

<210> SEQ ID NO 24
<211> LENGTH: 23
<212> TYPE: DNA
<213> ORGANISM: Artificial Sequence
<220> FEATURE:
<223> OTHER INFORMATION: reverse primer r2

<400> SEQUENCE: 24
ttaagtattg caacttactg agg                                       23

<210> SEQ ID NO 25
<211> LENGTH: 71
<212> TYPE: DNA
<213> ORGANISM: Artificial Sequence
<220> FEATURE:
<223> OTHER INFORMATION: human mitochondrial tRNA(Phe)
<220> FEATURE:

```
<221> NAME/KEY: ms2t6a
<222> LOCATION: (38)..(38)

<400> SEQUENCE: 25
gtttatgtag cttacctcct caaagcaata cactgaaaat gtttagacgg gctcacatca    60
ccccataaac a                                                         71

<210> SEQ ID NO 26
<211> LENGTH: 20
<212> TYPE: DNA
<213> ORGANISM: Artificial Sequence
<220> FEATURE:
<223> OTHER INFORMATION: forward primer

<400> SEQUENCE: 26
ctcctcaaag caatacactg                                                20

<210> SEQ ID NO 27
<211> LENGTH: 20
<212> TYPE: DNA
<213> ORGANISM: Artificial Sequence
<220> FEATURE:
<223> OTHER INFORMATION: reverse primer r1

<400> SEQUENCE: 27
agcccgtcta aacattttca                                                20

<210> SEQ ID NO 28
<211> LENGTH: 20
<212> TYPE: DNA
<213> ORGANISM: Artificial Sequence
<220> FEATURE:
<223> OTHER INFORMATION: reverse primer r2

<400> SEQUENCE: 28
gggtgatgtg agcccgtcta                                                20

<210> SEQ ID NO 29
<211> LENGTH: 69
<212> TYPE: DNA
<213> ORGANISM: Artificial Sequence
<220> FEATURE:
<223> OTHER INFORMATION: human mitochondrial tRNA(Ser)
<220> FEATURE:
<221> NAME/KEY: ms2t6a
<222> LOCATION: (34)..(34)

<400> SEQUENCE: 29
gaaaaagtca tggaggccat ggggttggct tgaaaccagc tttgggggt tcgattcctt     60 ccttttttg                                                            69

<210> SEQ ID NO 30
<211> LENGTH: 16
<212> TYPE: DNA
<213> ORGANISM: Artificial Sequence
<220> FEATURE:
<223> OTHER INFORMATION: forward primer

<400> SEQUENCE: 30
gaggccatgg ggttgg                                                    16

<210> SEQ ID NO 31
<211> LENGTH: 19
<212> TYPE: DNA
<213> ORGANISM: Artificial Sequence
```

```
<220> FEATURE:
<223> OTHER INFORMATION: reverse primer r1

<400> SEQUENCE: 31
cccaaagctg gtttcaagc                                                    19

<210> SEQ ID NO 32
<211> LENGTH: 18
<212> TYPE: DNA
<213> ORGANISM: Artificial Sequence
<220> FEATURE:
<223> OTHER INFORMATION: reverse primer r2

<400> SEQUENCE: 32
aatcgaaccc cccaaagc                                                     18

<210> SEQ ID NO 33
<211> LENGTH: 75
<212> TYPE: DNA
<213> ORGANISM: Artificial Sequence
<220> FEATURE:
<223> OTHER INFORMATION: human mitochondrial tRNA(Leu)
<220> FEATURE:
<221> NAME/KEY: ms2t6a
<222> LOCATION: (39)..(39)

<400> SEQUENCE: 33
gttaagatgg cagagcccgg taatcgcata aaacttaaaa ctttacagtc agaggttcaa       60
ttcctcttct taaca                                                        75

<210> SEQ ID NO 34
<211> LENGTH: 20
<212> TYPE: DNA
<213> ORGANISM: Artificial Sequence
<220> FEATURE:
<223> OTHER INFORMATION: forward primer

<400> SEQUENCE: 34
gcccggtaat cgcataaaac                                                   20

<210> SEQ ID NO 35
<211> LENGTH: 21
<212> TYPE: DNA
<213> ORGANISM: Artificial Sequence
<220> FEATURE:
<223> OTHER INFORMATION: reverse primer r1

<400> SEQUENCE: 35
cctctgactg taaagtttta a                                                 21

<210> SEQ ID NO 36
<211> LENGTH: 21
<212> TYPE: DNA
<213> ORGANISM: Artificial Sequence
<220> FEATURE:
<223> OTHER INFORMATION: reverse primer r2

<400> SEQUENCE: 36
ggaattgaac ctctgactgt a                                                 21
```

SIMPLE DETECTION METHOD FOR RNA MODIFICATION, AND METHOD FOR DETECTING TYPE-II DIABETES USING SAID DETECTION METHOD

This application is a National Stage of PCT/JP2014/055758 filed Mar. 6, 2014 which claims priority to Japanese Application Number 2013-150133 filed Jul. 19, 2013 and Japanese Application Number 2013-047278 filed Mar. 8, 2013. The entirety of the aforementioned applications is incorporated herein by reference.

TECHNICAL FIELD

The present invention relates to a method for detecting an RNA modification using a reverse transcription method. The present invention also relates to a method for detecting a modification in RNA using a combination of a reverse transcription method and a nucleic acid amplification method, such as a PCR method, and also quantitatively determining the modification level. More specifically, the present invention relates to a method in which reverse transcription is performed using at least two kinds of primers including a primer that binds to a region including an RNA modification site and a primer that complementarily binds to a region not including an RNA modification site, followed by nucleic acid amplification, such as PCR, thereby detecting and/or quantitatively determining the modification. The present invention also relates to a method for testing for genetic susceptibility to type 2 diabetes using the detection method.

BACKGROUND ART

Transfer RNA (tRNA) is an adapter molecule that decodes the information of mRNA (codon) and transfers the corresponding amino acid to a polypeptide chain being synthesized, and is a small-molecule RNA that plays a central role in protein translation. The anticodon loop of tRNA is chemically modified, which is necessary for the fidelity of translation. In particular, chemical modifications at the base at position 34, which is located in the anticodon, and the base at position 37, which is located in the vicinity of the anticodon, play an important role in controlling the accuracy of translation. In addition, it is believed that the breakdown of chemical modifications in the anticodon loop of tRNA is related to a disease.

Type 2 diabetes is a disease that occurs due to the combination of environmental factors and genetic factors. There are more than 200 million patients all over the world, and the number of patients is increasing in many countries. Type 2 diabetes is characterized by insulin resistance and/or abnormal insulin secretion in pancreatic β cells, but its main mechanism is still under discussion. Since 2007, large-scale genetic polymorphism epidemiological studies targeted at type 2 diabetes patients have been vigorously carried out around the world, and a large number of genetic single nucleotide polymorphisms (SNP) correlated with having diabetes have been identified. Among them, a large number of literatures have reported that SNPs of Cdkal1 (cdk5 regulatory associated protein 1-like 1) have the highest correlation with the onset of type 2 diabetes. It has also been revealed that a person carrying the risk allele of the Cdkal1 gene has poor glucose-responsive insulin secretion, but there is no correlation with obesity or insulin resistance. In addition, this genetic risk allele is common among Asians. Considering the phenotype of risk allele carriers, it is surmised that SNPs of Cdkal1 are involved in the onset of Asian type 2 diabetes.

Further, with respect to the physiological function of Cdkal1, it has been revealed that it is an enzyme that thiomethylates adenine[37] in tRNA corresponding to lysine into 2-methylthio-$N^6$-threonylcarbamoyladenosine ($ms^2t^6A$) (Nonpatent Document 1: Arragain S., et al., J. Biol. Chem., 285, 28425-28433 (2010) and Nonpatent Document 2: Tomizawa et al., Uehara Kinen Seimeikagaku Zaidan Kenkyu Houkokusyo (The Research Reports of the Uehara Memorial Foundation), 25 (2011), Article No. 77). It has been shown that $ms^2t^6A$ modification is necessary for accurate decoding of lysine codons (Nonpatent Document 1) and plays an important role in preventing the misreading of cognate codons, particularly in preventing misreading in the case where the translation rate is relatively high (Nonpatent Document 3: Tomizawa et al., Endocrine Journal 2011, 58 (10), 819-825).

It has been reported that in Cdkal1 knockout mice, mitochondria ATP production and first-phase insulin secretion are impaired. It has also been reported that pancreatic-β-cell-specific Cdkal1 knockout mice show the condition of type 2 diabetes, are observed to have pancreatic islet hypertrophy and impaired blood glucose control, and are hypersensitive to endoplasmic reticulum stress induced by high-fat diet (Nonpatent Document 3 and Nonpatent Document 4: Wei, F. Y. et al., J. Clin. Invest., 121, 3598-3608 (2011)).

That is, the present inventors have shown the following mechanism: when the expression or activity of Cdkal1 decreases due to genetic or environmental factors, the thiomethylation of lysine tRNA decreases, resulting in a decrease in the accuracy of insulin translation, which leads to the onset of type 2 diabetes. It has thus turned out that the thiomethylation of lysine tRNA is closely associated with the onset of diabetes. Meanwhile, thiomethylation is also present in mitochondrial tRNA encoded by mitochondrial DNA. It has been reported that the thiomethylation of mitochondrial tRNA is mediated by Cdk5rap1, and that a single nucleotide polymorphism mutation of the Cdk5rap1 gene is correlated with the onset of leukoplakia (Nonpatent Document 1 and Nonpatent Document 5: Reiter, V. et al., Nucleic Acids Res. 40, 6235-6240 (2012)). Like this, the thiomethylation of tRNA has been attracting attention as a new disease biomarker.

As a method for detecting the thiomethylation of tRNA, a detection method using a mass spectrometry method is generally used (Nonpatent Document 6: Suzuki, T. et al., Method. Enzymol., 425, 211-229 (2007)). In a mass spectrometry method, first, tRNA is purified from tissue or cells, and then tRNA is digested with nuclease into several oligonucleotides. Subsequently, the digested oligonucleotides are purified and analyzed by reversed-phase liquid chromatography and a mass spectrometer to detect thiomethylation. However, the detection of thiomethylation by mass spectrometry requires large amounts of RNA (in the unit of mg). Clinical samples are generally limited in amount, and it is difficult to obtain samples in the unit of mg. Accordingly, it is difficult to detect thiomethylation by mass spectrometry using clinical samples. In addition, the thiomethylation detection method by mass spectrometry requires a large number of pretreatments as described above. Therefore, there are problems in that it takes several days to detect thiomethylation, which not only makes it impossible to perform quick detection but also results in increased cost. Further, it is difficult to treat a large number of samples simultaneously. In addition, mass spectrometers are extremely expensive, and also the use thereof requires skills and experiences. Therefore, the analysis is difficult to perform in ordinary medical institutions or laboratories.

As described above, a mass spectrometry method takes time and cost, and further it is difficult to obtain large amounts of clinical samples. Because of these problems, a mass spectrometry method cannot be clinically applied as a method for detecting the thiomethylation of RNA. Therefore, there has been a demand for a novel detection method that is capable of detecting the thiomethylation of RNA efficiently, that is, quickly at low cost, and further allows for detection using a small amount of sample.

SUMMARY OF INVENTION

Technical Problems

An object of the present invention is to provide a method for detecting and/or quantitatively determining a modification present in RNA using a small amount of RNA sample. Another object of the present invention is to provide a method for detecting and/or quantitatively determining a modification present in tRNA, for example, thiomethylation.

Still another object of the present invention is to provide a method for detecting and/or quantitatively determining a modification present in RNA, thereby diagnosing a disease associated with the modification or the risk thereof. For example, an object is to provide a method for detecting and/or quantitatively determining the thiomethylation of lysine tRNA, thereby diagnosing human type 2 diabetes or the risk thereof.

Solution to Problems

The present inventors have conducted extensive research to achieve the above objects. As a result, they have found a method for detecting a modification (e.g., thiomethylation) in RNA (e.g., tRNA) using a reverse transcription method and a nucleic acid amplification method (e.g., quantitative PCR method) in combination, and thus accomplished the present invention.

The present invention is as follows.
(1) A method for detecting an RNA modification present in RNA, including performing the following two steps separately or simultaneously:
   a. a step of producing cDNA by reverse transcription of the RNA using a first primer, the first primer being an oligonucleotide designed to complementarily bind to a region including a site having the RNA modification on the RNA;
   b. a step of producing cDNA by reverse transcription of the RNA using a second primer, the second primer being an oligonucleotide designed to complementarily bind to a region on the upstream side (3' side) from a site having the RNA modification on the RNA, and
   measuring the difference between the amounts of cDNA produced in the respective steps, thereby detecting the RNA modification.
(2) The method according to (1) above, wherein the steps a and b are performed separately.
(3) The method according to (1) or (2) above, wherein the difference between the amounts of cDNA is measured by a nucleic acid amplification reaction method or a fluorescence method.
(4) The method according to (3) above, wherein the nucleic acid amplification reaction is a quantitative PCR method or a real-time quantitative PCR method.
(5) The method according to (4) above, wherein the difference between the amounts of cDNA is measured as a difference in the speed of nucleic acid amplification in the nucleic acid amplification reaction.
(6) The method according to any one of (1) to (5) above, wherein the RNA is tRNA.
(7) The method according to (6) above, wherein the RNA modification present in RNA is thiomethylation, methylation, or taurination present in tRNA.
(8) The method according to (7) above, wherein the thiomethylation present in tRNA is the thiomethylation of adenosine$^{37}$ in tRNA corresponding to Lys, tRNA corresponding to Trp, tRNA corresponding Phe, or tRNA corresponding to Ser (UCN).
(9) The method according to (8) above, wherein the thiomethylation present in tRNA is the thiomethylation of adenosine$^{37}$ in tRNA corresponding to Lys.
(10) The method according to any one of (1) to (9) above, wherein the RNA contains RNA derived from human tissue or human blood.
(11) The method according to (10) above, wherein the RNA contains RNA derived from human peripheral blood.
(12) A method for measuring the RNA modification rate of a sample, including performing the method according to any one of (1) to (11) above on at least two samples having known rates of RNA modification present in RNA and a sample having an unknown RNA modification rate, and comparing a parameter indicating a difference in cDNA amount measured from each sample with one another, thereby measuring the unknown RNA modification rate.
(13) The method according to (12) above, wherein the nucleic acid amplification reaction is a quantitative PCR method or a real-time quantitative PCR method, and the parameter is a difference in threshold cycle for amplifying target nucleic acids between using the first primer and the second primer.
(14) A method for measuring the RNA modification rate of a sample, including performing the method according to any one of (1) to (11) above on a sample having an unknown rate of RNA modification present in RNA, and comparing a parameter indicating a difference in cDNA amount measured from the sample with predetermined calibration curve, thereby measuring the unknown RNA modification rate.
(15) The method according to (14) above, wherein the nucleic acid amplification reaction is a quantitative PCR method or a real-time quantitative PCR method, and the parameter is a difference in threshold cycle for amplifying target nucleic acids between using the first primer and the second primer.
(16) A kit for detecting an RNA modification present in RNA in an RNA sample (e.g., sample derived from human tissue or human blood),
   the kit including:
   a first primer that is an oligonucleotide designed to complementary bind to a region including a site having the RNA modification on the RNA; and
   a second primer that is an oligonucleotide designed to complementary bind to a region on the 3' side from a site having the RNA modification on the RNA.
(17) The kit according to (16) above, wherein the RNA is tRNA.
(18) The kit according to (17) above, wherein the RNA modification present in RNA is thiomethylation present in tRNA.
(19) The kit according to (18) above, wherein the thiomethylation present in tRNA is the thiomethylation of adenosine$^{37}$ in tRNA corresponding to Lys, tRNA corresponding to Trp, tRNA corresponding Phe, or tRNA corresponding to Ser (UCN).

(20) The kit according to any one of (16) to (19) above, further including another primer for performing PCR.

(21) A method for using the method according to (9) above to determine whether a subject from which the tRNA is derived is a type 2 diabetes patient or has the risk thereof.

(22) The method according to (21) above, wherein the tRNA is derived from the subject's tissue or blood (preferably peripheral blood).

(23) A method for using the method according to (9) above to assay the insulin secretory capacity of a subject from which the tRNA is derived.

(24) The method according to (23) above, wherein the tRNA is derived from the subject's tissue or blood (preferably peripheral blood).

Advantageous of Invention

According to the present invention, RNA modifications, such as the thiomethylation of tRNA, can be detected quickly at low cost using a small amount of sample. Thus, it is useful as a detection method for various genetic abnormalities (e.g., without being limited thereto, genetic susceptibility to type 2 diabetes) using clinical samples (e.g., tissue or blood).

BRIEF DESCRIPTION OF DRAWINGS

FIG. 9c shows the percentage of non-ms$^2$-modified lysine tRNA (t$^6$A) in whole lysine tRNA (ms$^2$t$^6$A+t$^6$A).

DESCRIPTION OF EMBODIMENTS

Figure 1:
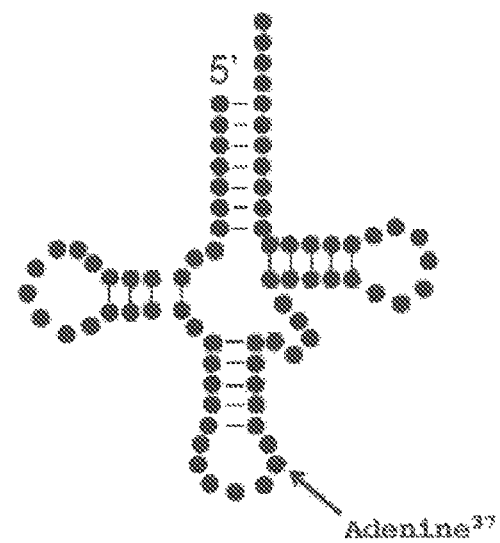
FIG. 1 The left figure shows tRNA corresponding to lysine, having adenine$^{37}$ thiomethylated. The right figure shows the thiomethylation reaction by Cdkal1.
Figure 1:
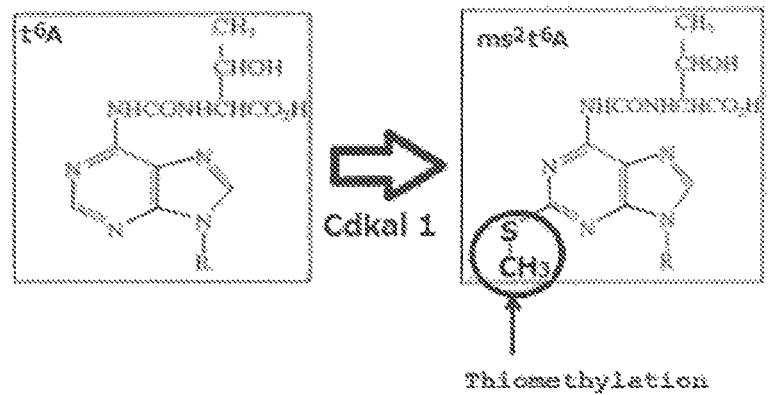

Hereinafter, the present invention will be described in further detail, but the present invention is not limited to these embodiments.

The present invention is characterized in that a modification present on RNA in an RNA sample is detected by reverse transcription using a first primer and a second primer. More specifically, it is characterized in that cDNA is produced by reverse transcription of RNA using a first primer, and the resulting amount of cDNA is compared with the amount of cDNA produced by reverse transcription of RNA using a second primer, thereby detecting a modification present on RNA.

In the detection method of the present invention, RNA is subjected to detection. Examples thereof include, but are not limited to, tRNA, rRNA, snRNA, mRNA-like ncRNA, snoRNA, and miRNA. tRNA, rRNA, and snRNA are preferable, and tRNA is more preferable.

In addition, tRNA to be subjected to detection is not particularly limited either. Examples thereof include tRNA corresponding to Lys, tRNA corresponding to Trp, tRNA corresponding to Phe, and tRNA corresponding to Ser (UCN).

In addition, "RNA sample" in the present invention is not particularly limited, and means a sample containing RNA regardless of the kind of RNA or its content. Examples of RNA samples include samples containing RNA derived from mammalian tissue, organ, or blood, such as RNA derived from human tissue, organ, or blood. It is preferable that the RNA sample is a sample containing RNA derived from human peripheral blood, which is easy to collect without excessive burden on the subject. The method for collecting leukocyte RNA from blood is not particularly limited. Examples thereof include a method in which whole blood is processed by Ficoll-Hypaque gradient centrifugation to concentrate leukocytes, followed by RNA extraction, and a method in which blood is collected in an RNA blood collecting tube, such as PAXgene blood collecting tube (manufactured by Nippon Becton Dickinson Company), and then, without separating leukocytes, directly used as an RNA sample according to the manufacturer's protocol.

In the detection method of the present invention, examples of RNA modifications that can be detected include, but are not limited to, thiomethylation, methylation, and taurination. Thiomethylation and methylation are preferable, and thiomethylation is more preferable. In the case of an RNA modification that is known or assumed to be associated with a specific disease, by detecting or quantitatively determining the modification using the method of the present invention, the presence or risk of the disease can be determined. For example, as already described, the thiomethylation of adenosine[37] in tRNA corresponding to lysine is associated with type 2 diabetes. Thus, by detecting or quantitatively determining such an RNA modification, the presence or risk of type 2 diabetes can be determined.

Examples of RNA modifications that can be detected by the method of the present invention and diseases known to be associated with the modifications (i.e., diseases whose presence or risk can be determined using the method of the present invention) include taurination and mitochondrial encephalomyopathy, thiomethylation and diabetes, and methylation and X-linked mental retardation.

The first primer used in the present invention is an oligonucleotide designed to complementary bind to a region including a site having the RNA modification to be detected by the detection method of the present invention (e.g., without being limited thereto, thiomethylated base). The length thereof is not particularly limited as long as it functions as a primer in a reverse transcription method and also in a PCR method combined therewith as necessary in the present invention, and is, for example, 10 or more bases, preferably 10 to 30 bases, and more preferably 15 to 20 bases. The region including a site having an RNA modification used in designing the oligonucleotide (primer) is not particularly limited as long as it includes the modification site. However, it is preferably selected such that the RNA modification site is located on the 5' side (from the center) of the region. When the first primer is designed in this manner, reverse transcription can be performed without being affected or with being less affected by the site having an RNA modification.

The second primer used in the present invention is an oligonucleotide designed to complementary bind to an arbitrary region on the upstream side (3' side) from a site having the RNA modification to be detected by the detection method of the present invention (e.g., without being limited thereto, thiomethylated base). The length thereof is not particularly limited as long as it functions as a primer in a reverse transcription method and also in a PCR method combined therewith as necessary in the present invention, and is, for example, 10 or more bases, preferably 10 to 30 bases, and more preferably 15 to 20 bases. Because the region to which the second primer complementary binds is located on the 3' side from a site having an RNA modification, in reverse transcription, the RNA modification (e.g., without being limited thereto, thiomethylation) inhibits reverse transcription. Accordingly, when reverse transcription is performed using the second primer designed as described above, an inversely proportional correlation is observed, in which the larger the amount of tRNA modified, the smaller the amount of reverse transcription product. Meanwhile, reverse transcription using the first primer produces cDNA independently of the RNA modification. Thus, the amount of cDNA produced using the second primer is smaller than the amount of cDNA produced using the first primer. The arbitrary region on the 3' side to which the second primer complementary binds is not particularly limited, and may be any region as long as reverse transcription is at least partially, preferably substantially, inhibited by the RNA modification in reverse transcription. However, it is preferable that the arbitrary region on the 3' side is designed to be not too far from or too close to the RNA modification site. For example, it is preferable that the region is designed to start about 3 to 10 bases away, preferably about 3 to 5 bases away, from the RNA modification site.

When the first primer and the second primer are designed in the positional relationship with the RNA modification site in this manner, the difference between the amounts of cDNA produced by reverse transcription using the respective primers will be more significant.

In addition, the first primer and/or second primer used in the present invention may be labeled with an appropriate labeling agent, such as a radioactive isotope, an enzyme, a fluorescent substance, or a luminescent substance. Examples of radioactive isotopes include $^{125}$I, $^{131}$I, $^{3}$H, and $^{14}$C. Examples of enzymes include glucosidase, alkali phosphatase, peroxidase, and malate dehydrogenase. Examples of fluorescent substances include fluorescein and Alex Fluor. Examples of luminescent substances include luminol.

The first and second primers used in the present invention can be designed to complementary bind to the target regions based on the RNA to be tested and the target RNA modification (its position and kind), and they can be synthesized in the usual manner using a DNA/RNA automatic synthesizer. Such first and second primers can each be dissolved in water or an appropriate buffer (e.g., TE buffer) to an appropriate concentration and stored at about −20° C.

For the detection of the difference between the amount of cDNA produced by the first primer and the amount of cDNA produced by the second primer, which is one of the features of the present invention, any method may be used as long as the difference can be detected. Examples thereof include nucleic acid amplification methods (nucleic acid amplification reaction) and mass spectrometry methods, and nucleic acid amplification methods are preferable. By using a nucleic acid amplification method, a difference in cDNA amount can be measured quickly at low cost. Incidentally, when fluorescently labeled nucleotides are used during reverse transcription, the subsequent detection of a difference in cDNA amount by a nucleic acid amplification method may be omitted. However, in terms of detection sensitivity and detection accuracy, it is preferable to combine a reverse transcription method and a nucleic acid amplification method.

Examples of nucleic acid amplification reactions include quantitative PCR and real-time quantitative PCR, and it is preferable to use an intercalation method using SYBR GREEN or a TaqMan® probe method. The use of these methods makes it possible to perform not only the detection of an RNA modification but also the comparison between measured samples and also the quantitative determination of the RNA modification. In addition, for the purpose of detection, when the first primer and the second primer are labeled with separate fluorescent substances and subjected to Multiplex analysis, the detection of an RNA modification can be performed quickly with fewer samples.

Primers to be used in the nucleic acid amplification reaction for amplifying cDNA produced using the first primer or the second primer are not particularly limited as long as they are a pair of primers that complementary bind to the produced cDNA, which is the reverse transcription product (reverse primer and forward primer). However, it is preferable that one of the primers is the same as the first primer.

In addition, the steps of producing cDNA by reverse transcription of RNA using the first and second primers and then amplifying the produced cDNA by real-time quantitative PCR according one embodiment of the present invention may be performed separately, or alternatively, it is also possible to perform one-step quantitative RT-PCR, in which PCR is performed using the same primer as the primer used for reverse transcription, and a reverse transcription reaction is also carried out in the real-time apparatus.

In the detection method of the present invention that combines a PCR method, the difference between the amount of cDNA produced by the first primer and the amount of cDNA produced by the second primer may be detected by observing the amplification of DNA over time (with an increase in the number of PCR cycles) or may also be detected as a difference in DNA amount in an arbitrary number of PCR cycles.

The RNA modification detection method that combines a reverse transcription method and a quantitative PCR method according to one embodiment of the present invention has extremely high detection sensitivity. For example, the presence of an RNA modification can be detected using only 1 ng of whole RNA, and its sensitivity is about 1000 times or more that of conventional mass spectrometry methods. In addition, because the method is a two-step RT-PCR method or a one-step RT-PCR method, where reverse transcription is followed by PCR, the detection operation can be completed within a short period of time, such as 2 to 3 hours, and it is also possible to treat a large number of samples simultaneously. Further, as compared with a mass spectrometry method, required instruments are less expensive, and also the operation is simple.

Another embodiment of the present invention is a kit for detecting an RNA modification present in RNA in an RNA sample. The kit contains a first primer, which is an oligonucleotide designed to complementary bind to a region including a site having an RNA modification, and a second primer, which is an oligonucleotide designed to complementary bind to a region on the 3' side from a site having an RNA modification. In addition, the kit contains the first and second primers, and may also contain other constituent components necessary for detection according to the detection method. For example, it may further contain other primers for performing a PCR method (forward primer and/or reverse primer) and a reaction buffer, DNA polymerase, or the like for performing PCR.

Still another embodiment of the present invention is a method for detecting thiomethylation present in tRNA in an RNA sample, characterized by using at least two primers that complementary bind to tRNA, that is, a first primer, which is an oligonucleotide designed to complementary bind to a region including the thiomethylated base to be detected, and an oligonucleotide designed to complementary bind to an arbitrary region on the 3' side from the thiomethylated base to be detected.

The first primer and the second primer can be designed without particular limitation as long as they satisfy the above conditions and each functions a primer in a reverse transcription method and also in a PCR method combined therewith as necessary in the present invention. The length thereof is not particularly limited, but can be designed to be, for example, 10 or more bases, preferably 10 to 30 bases, and more preferably 15 to 20 bases.

The first primer is designed to complementary bind to a region including the target thiomethylated base site as described above, and is more preferably designed such that the target thiomethylated base site is corresponding almost to the center of the primer. When reverse transcription is performed using this first primer, reverse transcription occurs independently of the thiomethyl group, and the amount of reverse transcription product is correlated with the total tRNA amount. Meanwhile, the second primer is designed to bind to the 3' side from the target thiomethylated base site, and thus the thiomethyl group at the thiomethylation site inhibits the efficiency of reverse transcription. Accordingly, when reverse transcription is performed using the second primer designed as described above, there is an inversely proportional correlation in which the larger the amount of tRNA thiomethylated, the smaller the amount of reverse transcription product. As a result, in correlation with the level of thiomethylation of tRNA, the amount of cDNA produced using the second primer is smaller the amount of cDNA produced using the first primer.

In yet another embodiment of the present invention, in the detection of thiomethylation, after reverse transcription, the difference between the amounts of cDNA produced by the first primer and the second primer can be further measured using the nucleic acid amplification method described above, such as real-time PCR (e.g., an intercalation method using SYBR GREEN or a TaqMan® probe method). In addition, as described above, both a two-step RT-PCR method and a one-step RT-PCR method can be used.

In a further embodiment of the present invention, provided is a method for using the method for detecting the thiomethylation of tRNA described above to detect the thiomethylation of tRNA derived from a subject (thiomethylation of adenine$^{37}$ in tRNA corresponding to lysine), thereby determining whether the subject is a type 2 diabetes patient or has the risk thereof. This allows for the accurate, simple, and quick testing for type 2 diabetes, and it is also possible to perform presymptomatic testing, risk testing, and early testing for type 2 diabetes.

In the present invention, "subject" is not particularly limited and includes type 2 diabetes patients, individuals susceptible to type 2 diabetes, and also healthy individuals.

In addition, by testing a sample collected from a patient who has developed type 2 diabetes using the testing method of the present invention, it is possible to determine the presence of an abnormality in the thiomethylation of tRNA as a cause of type 2 diabetes.

In a still further embodiment of the present invention, provided is a test kit for genetic susceptibility to type 2 diabetes. The kit contains at least a first primer, which is an oligonucleotide designed to complementary bind to a region including adenosine$^{37}$ in tRNA corresponding to lysine, and a second primer, which is an oligonucleotide designed to complementary bind to an arbitrary region on the 3' side from position 37 in tRNA corresponding to lysine.

As described above, the use of the detection method of the present invention makes it possible to detect an RNA modification (e.g., thiomethylation) within a short period of time, at low cost, and with high sensitivity. In addition, according to the present invention, it is possible to detect an RNA modification (e.g., thiomethylation of tRNA) using a small amount of RNA sample (e.g., tRNA from the peripheral blood of a test subject) to diagnose the onset risk of a disease (e.g., diabetes). Further, for patients, personalized medicine can be developed (treatments to suit the individual constitution, including the kind of therapeutic agent, the administration method, etc.).

EXAMPLES

Hereinafter, the present invention will be described in further detail with reference to the Examples. However, the present invention is not limited thereto.

Example 1: Detection of Thiomethylation of tRNA (1) Thiomethylation of tRNA Corresponding to Lysine (tRNA$^{Lys}$ (UUU))

Cdkal1, whose SNPs have been confirmed to have the highest correlation with the onset of type 2 diabetes, is an enzyme that thiomethylates adenosine$^{37}$ in tRNA corresponding to lysine into 2-methylthio-N$^6$-threonylcarbamoyladenosine (ms$^2$t$^6$A). FIG. 1 schematically shows thiomethyl-modified (37 A (ms$^2$)) lysine tRNA and the thiomethylation reaction by Cdkal1.

(2) Detection of tRNA$^{Lys}$ (UUU)

Figure 2:
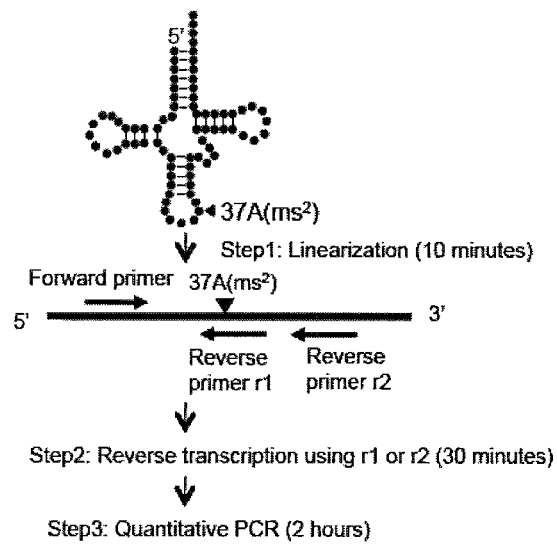
FIG. 2 The figure schematically shows the procedures of a reverse transcription method and a subsequent quantitative PCR method (qPCR-MtR method) in a method for detecting an RNA modification using first and second reverse primers according to one embodiment of the present invention, using lysine tRNA as a model.

FIG. 2 schematically shows the detection of tRNA$^{Lys}$ (UUU). Reverse transcription was performed using two reverse primers targeting the unique site of tRNA$^{Lys}$ (UUU) (thiomethylation site). The first reverse primer was designed to anneal to a specific region including the thiomethylation site (adenosine$^{37}$), and while the second reverse primer was designed to anneal to a specific sequence downstream in the 3' direction from the thiomethylation site. First, tRNA$^{Lys}$ (UUU) was linearized (Step1), and then reverse-transcribed using the first or second reverse primer (Step2). Subsequently, cDNA produced by the first reverse primer or the second reverse primer was amplified by quantitative PCR (Step3).

In the reverse transcription of fully modified tRNA$^{Lys}$ (UUU), the ms$^2$ modification of adenosine$^{37}$ attenuates reverse transcription. Thus, the amount of cDNA produced by the second reverse primer is smaller than the amount of cDNA produced by the first reverse primer. Meanwhile, in the case of partially modified tRNA$^{Lys}$ (UUU), with a decrease in the modification, the amount of cDNA produced by the second reverse primer approaches the amount of cDNA produced by the first reverse primer.

(3) Isolation of RNA (3-1) Isolation of Crude RNA

Whole RNA (crude RNA) was isolated from cells or tissue (mouse liver) by a guanidine thiocyanate/phenol/chloroform method using TRIzol reagent (Invitrogen) in accordance with the manufacturer's protocol.

(3-2) Purification of RNA

Individual tRNA$^{Lys}$ (UUU) was purified in accordance with the method described in Miyauchi, et al. Nucleic Acids Res., 35, e24 (2007) using a reciprocal circulating chromatography method (RCC).

(3-3) Isolation of RNA from Peripheral Blood

Whole RNA (crude RNA) was isolated from 1.5 ml of peripheral blood using QIAamp RNA Blood Mini Kit (Qiagen) in accordance with the manufacturer's protocol. Purified RNA was isolated from 50 ml of peripheral blood by adding excess hypotonic solution of QIAamp RNA Blood Mini Kit (Qiagen) to destroy erythrocytes, and then purifying whole RNA in leukocytes using TRIzol.

(4) Mass Spectrometry

Each isolated/purified tRNA (tRNA$^{Lys}$ (UUU), tRNA$^{Trp}$, tRNA$^{Phe}$, tRNA$^{Ser\ (UCN)}$, and tRNA$^{Leu\ (UUR)}$) was digested into oligonucleotides and then subjected to liquid chromatography/mass spectrometry in accordance with the method described in Wei et al. (Nonpatent Document 4).

(5) Primer

The following Table 1 shows the primer sequences designed to measure the ms$^2$ modification of tRNA$^{Lys}$ (forward primer sequence (SEQ ID NO: 2), first reverse primer sequence (reverse Primer r1) (SEQ ID NO: 3), and second reverse primer sequence (reverse Primer r2)(SEQ ID NO: 4)) together with the tRNA$^{Lys}$ sequence (SEQ ID NO: 1) (the ms$^2$ modification site adenosine$^{37}$ (A37) is indicated with an arrow).

TABLE 1

```
tRNA^Lys(UUU) (SEQ ID NO: 1)               ⇩
5'-GCCCGGATAGCTCAGTCGGTAGAGCATCAGACTTTTAATCTGAGGGTCCAGGGTTCAAGTCCCTGTTCGGGCG
HuMsLys_forward primer: GTCGSTAGAGCATCAGACTT (SEQ ID NO: 2)
HuMsLys_reverse primer r1: CCTGGACCCTCAGATTAAAA (SEQ ID NO: 3)
HuMsLys_reverse primer r2: GAACAGGGACTTGAACCCTG (SEQ ID NO: 4)
```

The following Table 2 shows the primer sequences designed to measure the ms$^2$ modification of mouse mitochondrial tRNA$^{Trp}$, tRNA$^{Phe}$, tRNA$^{Ser\ (UCN)}$, and tRNA$^{Leu\ (UUR)}$ (forward primer sequence, first reverse primer sequence (reverse Primer r1), and second reverse primer sequence (reverse Primer r2)) together with the respective tRNA sequences (the ms$^2$ modification site A37 is indicated with an arrow).

TABLE 2

```
tRNA^Trp: (SEQ ID NO: 5)                    ⇩
5'-AGAAGTTTAGGATATACTAGTCCGCGAGCCTTCAAAGCCCTAAGAAAACACACAAGTTTAACTTCTG

MsTrp_forward primer: GGATATACTAGTCCGCGAGC (SEQ ID NO: 6)
MsTrp_reverse primer r1: GTGTTTTCTTAGGGCTTTGA (SEQ ID NO: 7)
MsTrp_reverse primer r2: GTTAAACTTGTGTGTTTTCTTAG (SEQ ID NO: 8)

tRNA^Phe: (SEQ ID NO: 9)                    ⇩
5'-GTTAATGTAGCTTAATAACAAAGCAAAGCACTGAAAATGCTTAGATGGATAATTGTATCCCATAAACA

MsPhe_forward primer: GCTTAATAACAAAGCAAAGCA (SEQ ID NO: 10)
MsPhe_reverse primer r1: TATCCATCTAAGCATTTTCA (SEQ ID NO: 11)
MsPhe_reverse primer r2: TGGGATACAATTATCCATCT (SEQ ID NO: 12)
```

TABLE 2-continued tRNA$^{Ser(UCN)}$ (SEQ ID NO: 13)    ⇩
5'-GAGAAAGACATATAGGATATGAGATTGGCTTGAAACCAATTTTAGGGGGTTCGATTCCTTCCTTTCTTA
MsSerUCN_forward primer: CATATAGGATATGAGATTGGC (SEQ ID NO: 14)
MsSerUCN_reverse primer r1: AACCCCCTAAAATTGGTTTCA (SEQ ID NO: 15)
MsSerUCN_reverse primer r2: GAAGGAATCGAACCCCCTAA (SEQ ID NO: 16)

tRNA$^{Leu(UUR)}$: (SEQ ID NO: 17)    ⇩
5'-ATTAGGGTGGCAGAGCCAGGAAATTGCGTAAGACTTAAAACCTTGTTCCCAGAGGTTCAAATCCTCTCCCTAATA
MsLeuUUR_forward primer: AGCCAGGAAATTGCGTAAGA (SEQ ID NO: 18)
MsLeuUUR_reverse primer r1: CCTCTGGGAACAAGGTTTTA (SEQ ID NO: 19)
MsLeuUUR_reverse primer r2: AGGATTTGAACCTCTGGGAA (SEQ ID NO 20)

The following Table 3 shows the primer sequences designed to measure the ms$^2$ modification of human mitochondrial tRNA$^{Trp}$, tRNA$^{Phe}$, tRNA$^{Ser\ (UCN)}$, and tRNA$^{Leu\ (UUR)}$ (forward primer sequence, first reverse primer (reverse Primer r1) sequence, and second reverse primer (reverse Primer r2) sequence) together with the respective tRNA sequences (the ms$^2$ modification site A37 is indicated with an arrow).

TABLE 3 tRNA$^{Trp}$: (SEQ ID NO: 21)    ⇩
5'-AGAAATTTAGGTTAAATACAGACCAAGAGCCTTCAAAGCCCTCAGTAAGTTGCAATACTTAATTTCTG

HuTrp_forward primer: GGTTAAATACAGACCAAGAGC (SEQ ID NO: 22)
HuTrp_reverse primer r1: CAACTTACTGAGGGCTTTGAA (SEQ ID NO: 23)
HuTrp_reverse primer r2: TTAAGTATTGCAACTTACTGAGG (SEQ ID NO: 24)

tRNA$^{Phe}$: (SEQ ID NO: 25)    ⇩
5'-GTTTATGTAGCTTACCTCCTCAAAGCAATACACTGAAAATGTTTAGACGGGCTCACATCACCCCATAAACA

HuPhe_forward primer: CTCCTCAAAGCAATACACTG (SEQ ID NO: 26)
HuPhe_reverse primer r1: AGCCCGTCTAAACATTTTCA (SEQ ID NO: 27)
HuPhe_reverse primer r2: GGGTGATGTGAGCCCGTCTA (SEQ ID NO: 28)

tRNA$^{Ser(UCN)}$ (SEQ ID NO: 29)    ⇩
5'-GAAAAAGTCATGGAGGCCATGGGGTTGGCTTGAAACCAGCTTTGGGGGGGTTCGATTCCTTCCTTTTTTG
HuSerUCN_forward primer: GAGGCCATGGGGTTGG (SEQ ID NO: 30)
HuSerUCN_reverse primer r1: CCCAAAGCTGGTTTCAAGC (SEQ ID NO: 31)
HuSerUCN_reverse primer r2: AATCGAACCCCCCAAAGC (SEQ ID NO: 32)

tRNA$^{Leu(UUR)}$: (SEQ ID NO: 33)    ⇩
5'-GTTAAGATGGCAGAGCCCGGTAATCGCATAAAACTTAAAACTTTACAGTCAGAGGTTCAATTCCTCTTCTTAACA
HuLeuUUR_forward primer: GCCCGGTAATCGCATAAAAC (SEQ ID NO: 34)
HuLeuUUR_reverse primer r1: CCTCTGACTGTAAAGTTTTAA (SEQ ID NO: 35)
HuLeuUUR_reverse primer r2: GGAATTGAACCTCTGACTGTA (SEQ ID NO: 36)

(6) Reverse Transcription and Quantitative PCR (Sometimes Referred to as "qPCR-MtR" Herein when Used for the Detection of the Thiomethylation of tRNA)

Whole RNA (crude or purified RNA) isolated from cells or tissue (e.g., liver) was prepared to 100 ng/ml with RNase-free water unless otherwise noted. In order to avoid genomic contamination, in 20 μl of the reaction liquid, 2 μl (200 ng) of whole RNA was digested with 5 units of DNaseI (Roche) at 37° C. for 20 minutes and then treated at 75° C. for 10 minutes to heat-inactivate DNaseI. After the DNase treatment, 2.5 μl of the digested whole RNA was mixed with 1 μl of a solution containing 20 μM of the first reverse primer or second reverse primer, heat-denatured at 65° C. for 10 minutes, and then rapidly cooled on ice for at least 5 minutes. On ice, a recombinant reverse transcriptase (Transcriptor, Roche) was added to a final concentration of 0.5 units/μl. Reverse transcription was performed in the total reaction volume of 10 μl at 55° C. for 30 minute, followed by heat inactivation at 85° C. for 5 minutes. cDNA synthesized from the first or second reverse primer was subjected to quantitative PCR using SYBR Premix Ex Taq Kit (Takara) and ABI PRISM 7300 Real-Time PCR System (Applied biosystems) in accordance with the manufacturer's protocol.

(7) Knockout Mice and Cell Culture

Cdkal1 knockout mice were prepared in accordance with the method described in Wei, F. Y. et al., J. Clin. Invest., 121, 3598 to 3608 (2011) (Nonpatent Document 4). In order to remove the ubiquitous expression of Cdk5rap1, transgenic mice having exons 4 and 5 of Cdk5rap1 adjoined by the loxP sequence were interbreed with transgenic mice that express the Cre recombinase under the control of the CAG promotor. All the animal experiments were performed in accordance with the procedure manual approved by The Animal Ethics Committee of Kumamoto University (ID: B24-134, B24-132).

(8) Transfection

HeLa cells were cultured in a high-glucose-content DMEM culture medium (Invitrogen) containing 10% FBS. The transfection of siRNA was performed as follows. HeLa cells were seeded in a 24-well plate to a density of 30%. 24 hours later, siRNA targeting human Cdk5rap1 (Dharmacon)

or negative control siRNA (Ambion) were introduced into the cells using the Lipofectamine RNAiMAX reagent (Invitrogen) to a final concentration of 50 nM. Three days after transfection, whole RNA was isolated using the above method.

(9) Identification of Single Nucleotide Polymorphism (SNP) of Cdkal1

Using QIAamp DNA Blood Mini Kit (Qiagen), genomic DNA was purified from 200 µl of peripheral blood and prepared to 10 ng/µl with distilled water. SNP Cdkal1 (rs7754840) was tested using Taqman SNP Genotyping Assay Kit (Applied biosystems). Experiments using human genome samples were performed with approval of the Ethics Committee of Kumamoto University (Approval Number: Genome 159).

Figure 3:
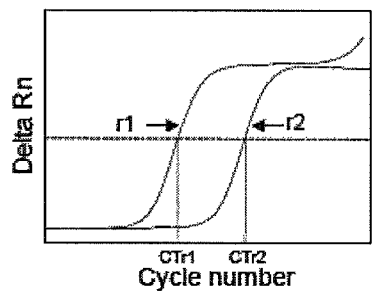
FIG. 3 The figure shows the results of the detection of the ms$^2$ modification of lysine tRNA by a reverse transcription method and a quantitative PCR method using lysine tRNA purified from wild-type mice and Cdkal1 KO mice.
Figure 3:
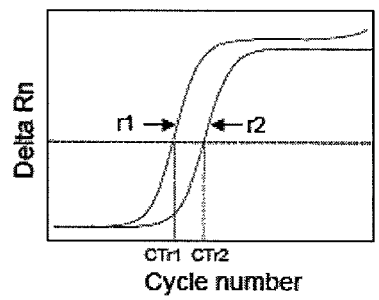

Example 2: Detection of ms² Modification Using Purified RNA of Wild-Type Mice and CadKal1 KO Mice In accordance with the RNA isolation method described above, tRNA$^{Lys}$ (UUU) with adenosine$^{37}$ fully ms²-modified was purified from the liver of wild-type mice, and tRNA$^{Lys}$ (UUU) whose ms² modification was completely stopped was purified from the liver of CadKal1 KO mice. Each purified tRNA$^{Lys}$ (UUU) was subjected to reverse transcription and then quantitative determination PCR. The results are shown in FIG. 3. FIG. 3a shows the results of qPCR-MtR performed using tRNA$^{Lys}$ (UUU) from wild-type mice, while FIG. 3b shows the results of qPCR-MtR performed using tRNA$^{Lys}$ (UUU) from CadKal1 KO mice.

In the case where fully ms²-modified wild-type tRNA$^{Lys}$ (UUU) was used as the template, the threshold cycle (CT) CTr2 obtained from the second reverse primer (r2) was remarkably larger than the threshold cycle CTr1 obtained from the first reverse primer (r1) (FIG. 3a). Meanwhile, in the case of tRNA$^{Lys}$ (UUU) lacking ms² modification, CTr2 was closer to CTr1. From these results, it was confirmed that in the case of using the second reverse primer, reverse transcription is reduced by the ms² modification of adenosine$^{37}$, while in the case of using the first reverse primer, reverse transcription is not affected. That is, it turned out that CTr2 reflects the level of ms² modification, and CTr1 reflects the entire tRNA molecules in the tRNA sample.

Example 3: Measurement of ms² Modification Rate in tRNA in Sample

Using a conventional ddCT method and the following calculation model, the difference between $CT_{r1}$ and $CT_{r2}$ in an arbitrary sample ($dCT_{r2r1}=CT_{r2}-CT_{r1}$) can be used as an index of modification rate. That is, the smaller the $dCT_{r2r1}$ value, the less the ms² modification of tRNA. In addition, based on the following calculation mathematical formula, the unknown ms² modification rate in tRNA in a test sample can be determined using two reference samples having known ms² modification rates in tRNA.

[Mathematical formula 1]

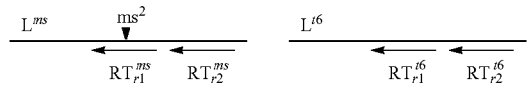

$L^{ms}$ represents the total number of tRNA molecules with ms² modification, $L^{t6}$ represents the total number of tRNA molecules without ms² modification, and $L^{total}$ represents the total number of RNA molecules. Accordingly, the absolute modification rate (x) is shown by the following mathematical formula.

[Mathematical formula 2]

$$L^{total} = L^{ms} + L^{t6}, \quad (1)$$

$$x = \frac{L^{ms}}{L^{total}}, \quad 1-x = \frac{L^{t6}}{L^{total}}, \quad 0 \le x \le 1 \quad (2)$$

During reverse transcription, tRNA with ms² modification is transcribed with the first reverse primer (r1) or the second reverse primer (r2) at the rate $RT^{ms}_{r1}$ or $RT^{ms}_{r2}$. Meanwhile, tRNA without ms² modification is transcribed with the first reverse primer (r1) or the second reverse primer (r2) at the rate $RT^{t6}_{r1}$ or $RT^{t6}_{r2}$. Reverse transcription with r1 is not related to ms² modification and thus is shown by the following mathematical formula (3), while reverse transcription with r2 is reduced by ms² modification and thus is shown by the following mathematical formula (4).

[Mathematical formula 3]

$$RT^{ms}_{r1} = RT^{t6}_{r1} = RT_{r1} \quad (3)$$

$$RT^{ms}_{r2} < RT^{t6}_{r2}, \quad \frac{RT^{ms}_{r2}}{RT^{t6}_{r2}} = D, \quad 0 < D < 1 \quad (4)$$

When reverse transcription is performed using a whole RNA sample including $L^{ms}$ and $L^{t6}$, the transcription can be represented as in the following mathematical formulae (5) to (7).

[Mathematical formula 4]

$$R_0 = RT^{ms}_{r1} \cdot L^{ms} + RT^{t6}_{r1} \cdot L^{t6} = RT_{r1} \cdot L^{total}, \quad (5)$$

$$M_0 = RT^{ms}_{r2} \cdot L^{ms} + RT^{t6}_{r2} \cdot L^{t6} = (x \cdot RT^{ms}_{r2} + (1-x) \cdot RT^{t6}_{r2}) \cdot L^{total}, \quad (6)$$

If $x=a$, then $M_{0a} = (a \cdot RT^{ms}_{r2} + (1-a) \cdot RT^{t6}_{r2}) \cdot L^{total}$,
$R_{0a} = RT_{r1} \cdot L^{total} \quad (7)$ Here, $R_0$ and $M_0$ are the amounts of cDNA produced using the primers r1 and r2, respectively. $R_{0a}$ and $M_{0a}$ are the amounts of cDNA produced by the primers r1 and r2, respectively, using a whole RNA sample having a modification rate a. The following mathematical formula (8) shows exponential amplification by the subsequent PCR.

[Mathematical formula 5]

$$X_T = X_0 \cdot (1+E)^{CT_x}, \text{ thus } X_0 = X_T (1+E)^{-CT_x}, \quad (8)$$

Here, $X_T$ is the threshold number of target molecules, $CT_x$ is the threshold cycle for target amplification, and E is the efficiency of target amplification.

During PCR using cDNA produced by the primer r1 or r2 from an arbitrary sample having a modification rate a, the reaction can be shown by the following relational expression (9).

[Mathematical formula 6]

$$M_{0a} = M_T (1+E)^{-CT_{r2a}}, \quad R_{0a} = R_T (1+E)^{-CT_{r1a}} \quad (9)$$

$M_{Oa}$ is divided by $R_{Oa}$ to give the following mathematical formula (10).

[Mathematical formula 7]

$$r_a = \frac{M_{oa}}{R_{oa}} = \frac{M_T}{R_T} \cdot (1+E)^{-(CT_{r2a}-CT_{r1a})} = \frac{M_T}{R_T} \cdot (1+E)^{-dCT_{r2a-r1a}}, \quad (10)$$

$$-(CT_{r2a} - CT_{r1a}) = -dCT_{r2ar1a}$$

Here, $CT_{r2a}$ CT is the threshold cycle for amplification of $M_{Oa}$ produced by the primer r2, while $CT_{r1a}$ is the threshold cycle for amplification of $R_{Oa}$ produced by the primer r1.

The comparison between samples having modification rates a and b gives the following mathematical formula (11).

[Mathematical formula 8]

$$\frac{r_b}{r_a} = (1+E)^{-(dCT_{r2br1b}-dCT_{r2ar1a})} = (1+E)^{-ddCT_{ba}}, \quad (11)$$

$$-(dCT_{r2br1b} - dCT_{r2ar1a}) = -ddCT_{ba}$$

Meanwhile, from the mathematical formula (4) and the mathematical formula (7), the following mathematical formula (12) is given.

[Mathematical formula 9]

$$\frac{r_b}{r_a} = \frac{M_{ob}}{R_{ob}} \cdot \frac{R_{oa}}{M_{oa}} = \frac{b \cdot \frac{RT_{r2}^{ms}}{RT_{r2}^{t6}} + (1-b)}{a \cdot \frac{RT_{r2}^{ms}}{RT_{r2}^{t6}} + (1-a)} = \frac{1-b(1-D)}{1-a(1-D)} \quad (12)$$

From individuals having modification rates w, k, and s, respectively, the following mathematical formula (13) is derived.

[Mathematical formula 10]

$$\frac{r_w}{r_k} = (1+E)^{-(dCT_{r2wr1w}-dCT_{r2kr1k})} = (1+E)^{-ddCT_{wk}} \quad (13)$$

$$\frac{r_s}{r_k} = (1+E)^{-(dCT_{r2sr1s}-dCT_{r2kr1k})} = (1+E)^{-ddCT_{sk}}, \text{ then}$$

$$s = \frac{1-(1+E)^{-ddCT_{sk}}}{1-(1+E)^{-ddCT_{wk}}} w + \frac{(1+E)^{-ddCT_{sk}}-(1+E)^{-ddCT_{wk}}}{1-(1+E)^{-ddCT_{wk}}} k$$

If the modification rates w and k are already known, the modification rate s can be determined from the mathematical formula (13). Even in the case where the modification rate w, k, and s are unknown, the relative comparison of the modification rates can be easily made using $dCT_{r2r1}$ as shown by the following mathematical formula.

[Mathematical formula 11]

$$\frac{r_w}{r_w} = (1+E)^{-ddCT_{ww}} = 1$$

$$\frac{r_k}{r_w} = (1+E)^{-ddCT_{kw}},$$

$$\frac{r_s}{r_w} = (1+E)^{-ddCT_{sw}}$$

If $k > w > s$, then $$(1+E)^{-ddCT_{kw}} < (1+E)^{-ddCT_{ww}} = 1 < (1+E)^{-ddCT_{sw}}$$

$$ddCT_{kw} > ddCT_{ww} = 0 > ddCT_{sw}$$

$$dCT_{r2kr1k} - dCT_{r2wr1w} >$$

$$dCT_{r2wr1w} - dCT_{r2wr1w} > dCT_{r2sr1s} - dCT_{r2wr1w}$$

$$\therefore dCT_{r2kr1k} > dCT_{r2wr1w} > dCT_{r2sr1s}$$

Example 4: Measurement of tRNA with Various $ms^2$ Modification Rates

Using the principle of the present invention, tRNA samples having various $ms^2$ modification rates were subjected to measurement. Purified $tRNA^{Lys}$ (UUU) from wild-type mice and purified $tRNA^{Lys}$ (UUU) from CadKal1 KO mice were combined in the ratios shown in the table to prepare tRNA having various $ms^2$ modification rates (25, 50, 75, and 100%), and they were subjected to qPCR-MtR. The ddCT value was calculated by subtracting the $dCT_{r2r1}$ value of each sample from the $dCT_{r2r1}$ value of Sample 1. The calculated modification rate was calculated in accordance with the mathematical formula of Example 3. The results are shown in the following Table 4.

TABLE 4

| Sample No. | Ratio of Sample (WT:KO) | ddCT | 2^(-ddCT) | calculated rate | Expected rate |
|---|---|---|---|---|---|
| 1 | 0:100 | 0 | 1.00 | 0.000000 | 0.00 |
| 2 | 25:75 | 0.17 | 0.889 | 0.1145437 | 0.25 |
| 3 | 50:50 | 0.67 | 0.629 | 0.3828109 | 0.50 |
| 4 | 75:25 | 1.79 | 0.289 | 0.7324833 | 0.75 |
| 5 | 100:0 | 5.08 | 0.030 | 1.000000 | 1.00 |

Figure 4:
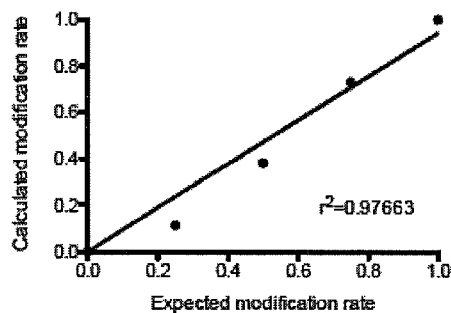
FIG. 4 The figure shows the results of using purified RNA, wherein the calculated modification rate (calculated rate) is plotted on the Y-axis, while the expected modification rate (expected rate) on the X-axis.

The ordinary dCT value decreased with a decrease in the $ms^2$ modification rate. In addition, using a fully $ms^2$-modified tRNA sample (Sample No. 5) and a tRNA sample without $ms^2$ modification (Sample No. 1) as references, the calculated modification rates of partially $ms^2$-modified samples (Samples Nos. 2 to 4) were compared with respective expected modification rates. As a result, it turned out that an expected value can be precisely predicted from the calculated value (FIG. 4). Accordingly, it turned out that the unknown tRNA modification rate of a sample can be measured using reference samples having known tRNA modification rates or using a standard calibration curve previously determined.

Example 5: Measurement of $ms^2$ Modification Using Crude RNA

Figure 5:
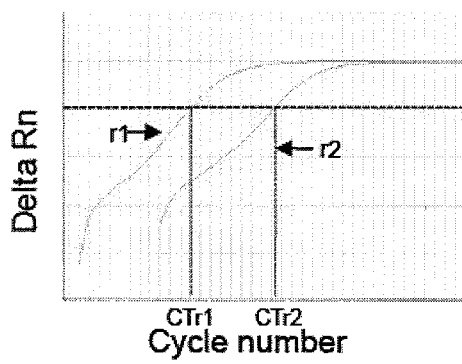
FIG. 5 The figure shows the results of the detection of the ms$^2$ modification of lysine tRNA by reverse transcription and a quantitative PCR method using crude RNA isolated from wild-type mice and Cdkal1 KO mice.
Figure 5:
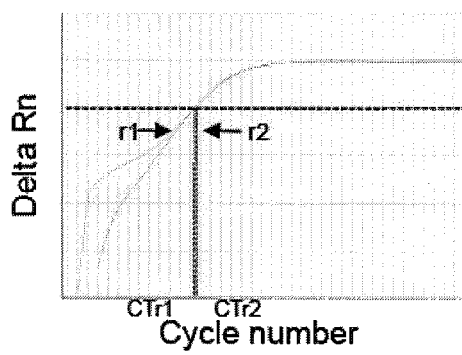

Using a small amount of crude RNA, $ms^2$ modification was measured by qPCR-MtR. 200 ng of whole RNA was isolated from wild-type mice and also from CadKal1 KO mice and qPCR-MtR was performed using the first or second reverse primer. The results are shown in FIG. 5. FIG. 5a shows the results of qPCR-MtR performed using crude RNA from wild-type mice, while FIG. 5b shows the results of qPCR-MtR using crude RNA from CadKal1 KO mice. The results agree with the results of the experiment using purified $tRNA^{Lys}$ (UUU), and the $CT_{r2}$ value obtained from the whole RNA from CadKal1 KO mice was significantly lower than the $CT_{r2}$ value obtained from the whole RNA from wild-type mice.

Further, in the same manner as in Example 4, whole RNA (crude RNA) from wild-type mice and whole RNA (crude RNA) from CadKal1 KO mice were combined at specific ratios to prepare RNA having various $ms^2$ modification rates (25, 50, 75, and 100%), and they were subjected to qPCR-MtR. The $dCT_{r2r1}$ value of each sample is standardized based on the $dCT_{r2r1}$ value of Sample 1 and shown as a ddCT value. The results are shown in the following Table 5.

TABLE 5

| Sample No. | Ratio of Sample (WT:KO) | ddCT | 2^(-ddCT) | calculated rate | Expected rate |
|---|---|---|---|---|---|
| 1 | 0:100 | 0 | 1.000 | 0.000000 | 0.00 |
| 2 | 25:75 | 0.4771 | 0.718 | 0.2844918 | 0.25 |
| 3 | 50:50 | 1.1245 | 0.459 | 0.5469375 | 0.50 |
| 4 | 75:25 | 2.9289 | 0.131 | 0.8776691 | 0.75 |
| 5 | 100:0 | 6.6102 | 0.010 | 1.000000 | 1.00 |

Figure 6:
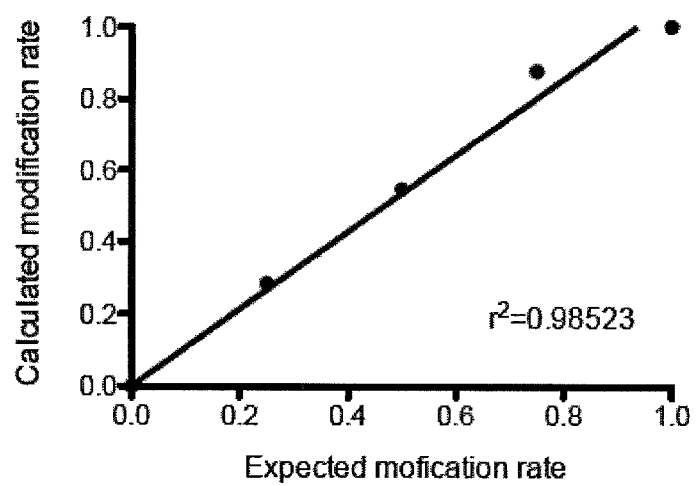
FIG. 6 The figure shows the results of using crude RNA, wherein the calculated modification rate (calculated rate) is plotted on the Y-axis, while the expected modification rate (expected rate) on the X-axis.

The dCT value decreased with a decrease in the $ms^2$ modification rate. In addition, using a fully $ms^2$-modified tRNA sample (Sample No. 5) and a tRNA sample without $ms^2$ modification (Sample No. 1) as references, the calculated modification rates of partially $ms^2$-modified samples (Samples Nos. 2 to 4) were compared with respective expected modification rates. As a result, it turned out that an expected value can be precisely predicted from the calculated value (FIG. 6). Accordingly, it turned out that even in the case of using whole RNA, the unknown tRNA modification rate of a sample can be measured using reference samples having known modification rates or using a standard calibration curve previously determined.

Example 6: Measurement of $ms^2$ Modification Using Small Amount of Crude RNA

Figure 7:
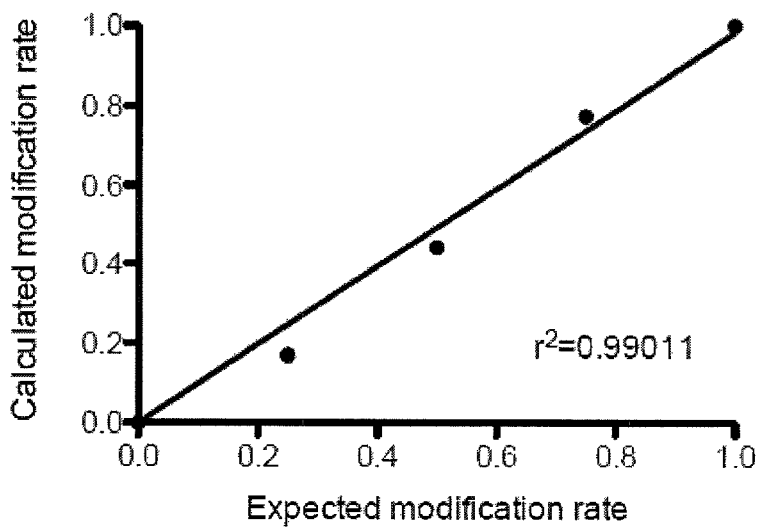
FIG. 7 The figure shows the results of the detection of the ms$^2$ modification of lysine tRNA by reverse transcription and a quantitative PCR method using crude RNA (2 ng) isolated from wild-type mice and Cdkal1 KO mice, wherein the calculated modification rate (calculated rate) is plotted on the Y-axis, while the expected modification rate (expected rate) on the X-axis.

The measurement was performed in the same manner as in Example 5. However, the amount of whole RNA used was 2 ng. Whole RNA obtained from wild-type mice and Cad-Kal1 KO mice was prepared to 1 ng/μl and subjected to qPCR-MtR using the first or second reverse primer. The results are shown in Table 6 and FIG. 7 below. It turned out that sufficient detection is possible even the amount of RNA is 2 ng.

TABLE 6

| Sample No. | Ratio of Sample (WT:KO) | ddCT | 2^(-ddCT) | calculated rate | Expected rate |
|---|---|---|---|---|---|
| 1 | 0:100 | 0.000 | 1.000 | 0.000 | 0.000 |
| 2 | 25:75 | 0.227 | 0.885 | 0.169 | 0.250 |
| 3 | 50:50 | 0.691 | 0.619 | 0.442 | 0.500 |
| 4 | 75:25 | 1.585 | 0.333 | 0.774 | 0.750 |
| 5 | 100:0 | 2.848 | 0.139 | 1.000 | 1.000 |

Example 7: Measurement Using RNA Sample from Peripheral Blood

Figure 8:
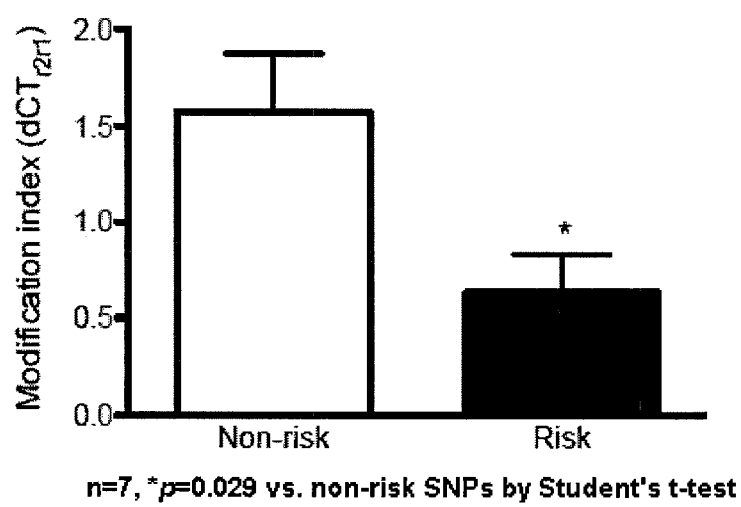
FIG. 8 The figure shows the results of the detection of the ms$^2$ modification of lysine tRNA by reverse transcription and a quantitative PCR method using crude RNA from the peripheral blood of individuals carrying the Cdkal1 SNP (rs775840) type 2 diabetes-related risk allele (Risk group) and healthy individuals (individuals carrying no Cdkal1 SNP risk allele) (Non-risk group).

Peripheral blood was collected from individuals carrying the Cdkal1 SNP (rs775840) type 2 diabetes-related risk allele and healthy individuals (individuals carrying no Cdkal1 SNP risk allele) and subjected to the following experiment. Using 100 ng of whole RNA (crude RNA) isolated from a peripheral blood sample, qPCR-MtR was performed using the first or second reverse primer. Because references, for determining the absolute $ms^2$ modification rate of human $tRNA^{Lys}$ (UUU) are not available, a $dCT_{r2r1}$ value was used to measure the relative modification level. The $dCT_{r2r1}$ values of whole RNA isolated from 1.5 ml of the peripheral blood of individuals carrying the type 2 diabetes-related risk allele of Cdkal1 SNP (rs775840) (population size: 6) and healthy individuals (population size: 7) were compared as modification indexes. The results are shown in FIG. 8. The $dCT_{r2r1}$ value of individuals carrying the risk allele of Cdkal1 SNP was significantly lower than the $dCT_{r2r1}$ value of healthy individuals. This shows that $ms^2$ modification is suppressed in individuals carrying the type 2 diabetes-related Cdkal1 SNP.

Figure 9:
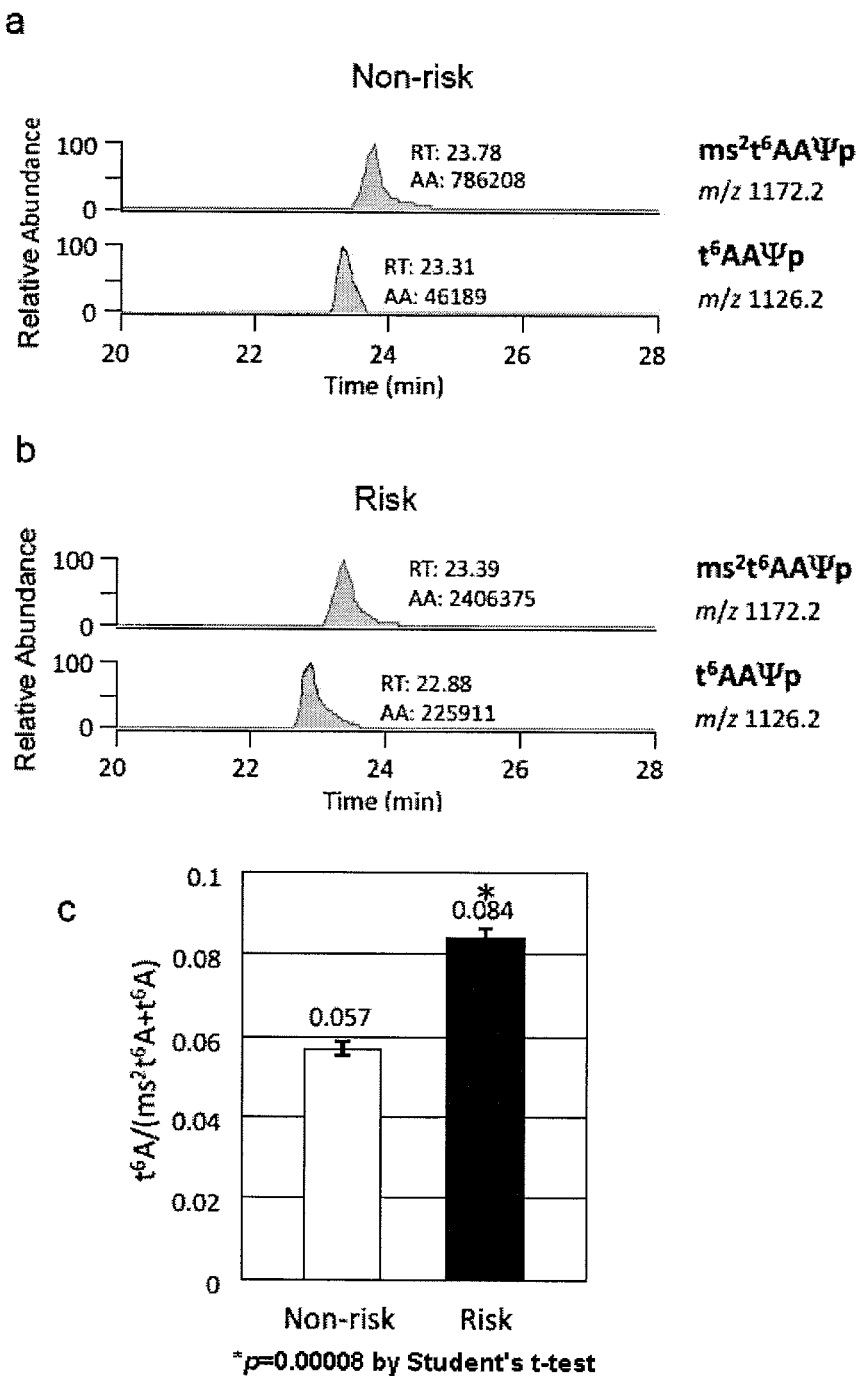
FIG. 9 The figure shows the results of mass spectrometry using purified RNA from the peripheral blood of individuals carrying the Cdkal1 SNP (rs775840) type 2 diabetes-related risk allele (FIG. 9b) and healthy individuals (individuals carrying no Cdkal1 SNP risk allele) (FIG. 9a).

The results of qPCR-MtR were confirmed by mass spectrometry. Using 50 μg of whole RNA isolated from 30 ml of the peripheral blood of individuals carrying the risk allele of Cdkal1 SNP and healthy individuals, $tRNA^{Lys}$ (UUU) was purified, and purified $tRNA^{Lys}$ (UUU) was subjected to mass spectrometry. The results are shown in FIG. 9. FIG. 9b shows the results from individuals carrying the risk allele, while FIG. 9a shows the results from healthy individuals (mass chromatogram: $ms^2t^6A$ (m/z459), $t^6A$ (m/z413)). The non-modification rate was standardized as the ratio of the $t^6A$ area relative to the total area of $t^6A$ and $ms^2t^6A$. The average of three experiments using whole RNA isolated from the same individuals is shown. As shown in FIG. 9c, the non-$ms^2$-modified $tRNA^{Lys}$ (UUU) in individuals carrying the risk allele was 1.47 times greater.

Example 8: Measurement Using Mitochondrial tRNA Sample

Mitochondrial tRNA of mammals also have 2-methylthio-$N^6$-threonylcarbamoyladenosine ($ms^2t^6A$) modification. In mitochondrial tRNA, $tRNA^{Trp}$, $tRNA^{Phe}$, and $tRNA^{Ser\ (UCN)}$ have $ms^2t^6A$ modification, but $tRNA^{Leu\ (UUR)}$ does not have $ms^2t^6A$ modification. In mammalian cells, Cdk5rap1 converts $N^6$-isopentenyladenosine ($i^6A$) into $ms^2i^6A$ at A37.

The $ms^2i^6A$ modification of mitochondrial tRNA in Cdk5rap1 knockout (Cdk5rap1 KO) mice was systematically examined by qPCR-MtR using the first or second reverse primer. Whole RNA (crude RNA) was prepared from wild-type mice and Cdk5rap1 KO mice and, using the primers shown in Table 3 above, each measured for the $dCT_{r2r1}$ values of $tRNA^{Trp}$, $tRNA^{Phe}$, $tRNA^{Ser\ (UCN)}$, and $tRNA^{Leu\ (UUR)}$.

The results are shown in the following Table 7. The $dCT_{r2r1}$ values of $tRNA^{Trp}$, $tRNA^{Phe}$, and $tRNA^{Ser\ (UCN)}$ of wild-type mice (WT) were significantly higher than the $dCT_{r2r1}$ values obtained from Cdk5rap1 KO mice. This shows that the $ms^2$ modification of $tRNA^{Trp}$, $tRNA^{Phe}$, and $tRNA^{Ser\ (UCN)}$ is suppressed in knockout mice. Meanwhile, the $dCT_{r2r1}$ value of $tRNA^{Leu\ (UUR)}$ of wild-type mice was almost the same as the $dCT_{r2r1}$ value obtained from Cdk5rap1 KO mice.

TABLE 7

| | dCt | | | |
|---|---|---|---|---|
| | tRNA$^{Trp}$ | tRNA$^{Phe}$ | tRNA$^{Ser(UCN)}$ | tRNA$^{Leu(UUR)}$ |
| WT | 2.053 | 2.466 | 0.620 | 0.369 |
| Cdk5rap1 KO | 0.252 | −0.404 | 0.0001 | 0.360 |
| p value | 0.000004 | 0.00004 | 0.0005 | 0.097 | n = 3, Student's t-test was performed to examine the statistical significance.

Figure 10:
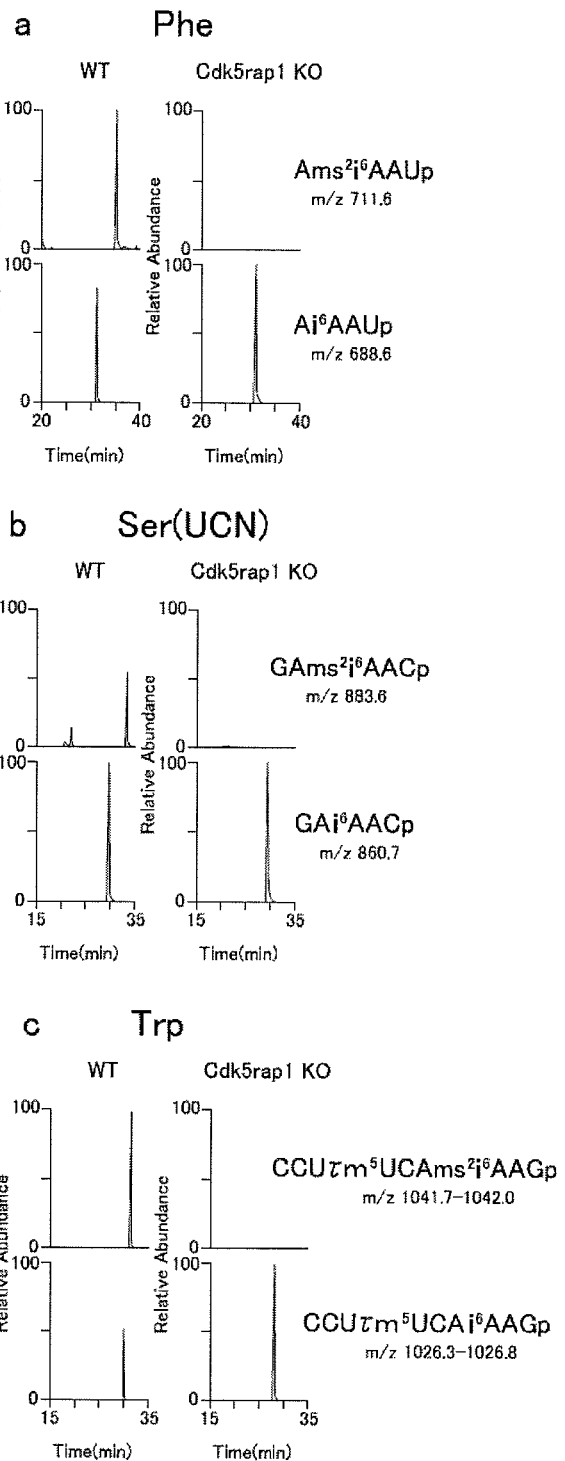
FIG. 10 The figure shows the results of the mass spectroscopy of the ms$^2$ modification of A37 in mitochondrial tRNA. The upper sides show the mass chromatograms of ms$^2$-modified oligonucleotides, while the lower sides show those of non-ms$^2$-modified oligonucleotides.

In addition, with respect to each of mitochondrial tRNA$^{Trp}$, tRNA$^{Phe}$, and tRNA$^{Ser\ (UCN)}$ isolated and purified from the liver of wild-type mice and Cdk5rap1 KO mice, ms$^2$ modification was checked by mass spectrometry. As a result, it was observed that ms$^2$ modification of tRNA$^{Trp}$, tRNA$^{Phe}$, and tRNA$^{Ser\ (UCN)}$ had disappeared, and the results agreed with the results of qPCR-MtR. The results are shown in FIG. 10.

Example 9: Measurement of ms$^2$ Modification of tRNA Using HeLa Cells

HeLa cells having introduced therein siRNA against Cdk5rap1 (KD) and HeLa cells having introduced therein control siRNA (Control) were prepared, and crude RNA was isolated from each of the cells in accordance with the method described in Example 1. Using the isolated crude RNA, qPCR-MtR was performed using the first or second reverse primer, and the dCT$_{r2r1}$ values of tRNA$^{Trp}$, tRNA$^{Phe}$, tRNA$^{Ser\ (UCN)}$, and tRNA$^{Leu\ (UUR)}$ were measured. The results are shown in the following Table 8.

TABLE 8

| tRNA species | tRNA$^{Trp}$ | tRNA$^{Phe}$ | tRNA$^{Ser(UCN)}$ | tRNA$^{Leu(UUR)}$ |
|---|---|---|---|---|
| Control (dCT) | 3.733 | 2.702 | 2.175 | 0.333 |
| KD (dCT) | 0.233 | −0.359 | −1.359 | 0.566 |
| p value | p = 0.00002 | p = 000186 | p = 0.00002 | p = 0.1 | n = 3, Student's t-test was performed to examine the statistical significance.

Also in the results of using HeLa cells, similarly to the results of using mice, the dCT$_{r2r1}$ values of tRNA$^{Trp}$, tRNA$^{Phe}$, and tRNA$^{Ser\ (UCN)}$ obtained from the Control cells were significantly higher than the dCT$_{r2r1}$ values obtained from the Cdk5rap1 knockdown (KD) cells. Meanwhile, the dCT$_{r2r1}$ value of Control tRNA$^{Leu\ (UUR)}$ was almost the same as the dCT$_{r2r1}$ value of Cdk5rap1 KD.

Example 10: Examination of Correlation Between Cdcak1 Gene Mutation and Modification of tRNA$^{Lys}$ (UUU)

Figure 11:
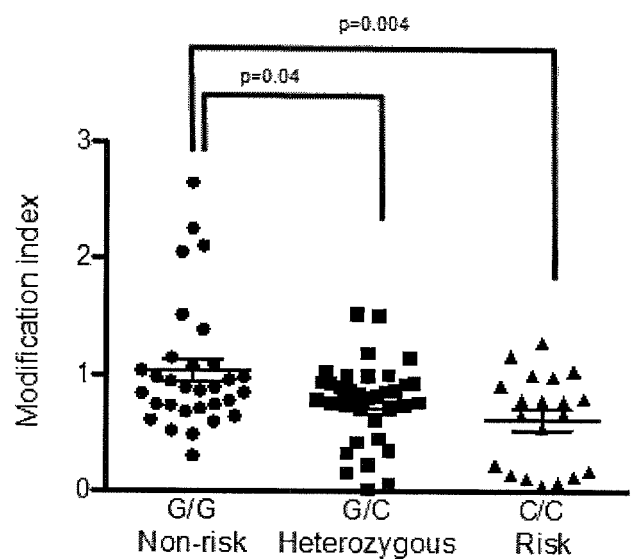
FIG. 11 The figure shows the level of thiomethylation modification of lysine RNA in each of groups having the Cdkal1 gene mutation (group homozygous for the mutation (C/C) and group heterozygous for the mutation (G/C)) and a group not having the mutation (G/G).

In accordance with Example 1, DNA and RNA were extracted from human peripheral blood. In accordance with the method of Example 1 (9), the Cdkal1 gene mutation related to the onset of diabetes was identified, and samples were divided into a group homozygous for the risk Cdkal1 gene mutation (C/C, n=20), a group homozygous for the non-risk Cdkal1 gene mutation (G/G, n=31), and a hetero group (G/C, n=35). Next, a PCR method was performed using RNA of each group to measure the modification of tRNA$^{Lys}$ (UUU), and the relative modification rates were examined. The results are shown in FIG. 11. As a result, in the group having the risk Cdkal1 gene mutation that increases the risk of the onset of diabetes, the thiomethylation modification rate was significantly lower than in the group having the non-risk Cdkal1 mutation. P<0.05 is regarded as significant. ANOVA was used for assay.

Figure 12:
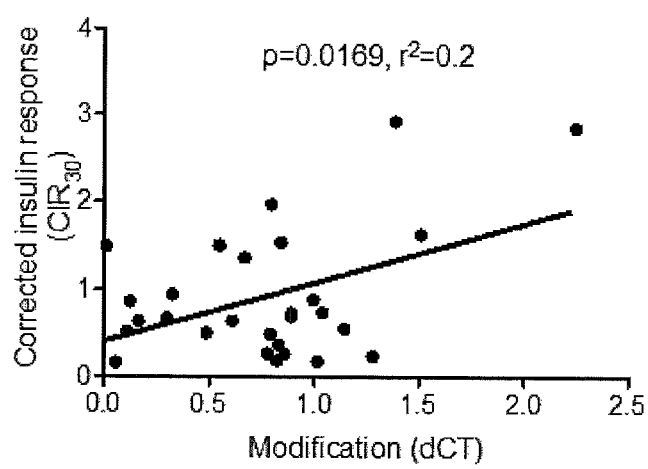
FIG. 12 The figure shows the correlation between the level of thiomethylation modification of lysine tRNA and insulin secretory capacity.

Example 11: Examination of Correlation Between Thiomethylation and Insulin Secretory Capacity In order to examine the correlation between the thiomethylation of tRNA$^{Lys}$ (UUU) and insulin secretory capacity, carbohydrate tolerance testing was performed on humans in the usual manner. A solution containing 75 g of glucose (Trelan-G) was administered to 28 volunteers fasted overnight (Cdkal1 mutation genotype: C/C, n=9; G/C, n=12; G/G, n=7). Blood was collected before and 30 minutes after the administration, and the insulin secretory capacity (corrected insulin response) was calculated based on the blood insulin and the blood sugar level. In addition, RNA was purified from the same blood samples. The level of thiomethylation modification was detected by a qPCR-MtR method, and the correlation between insulin secretory capacity and thiomethylation level was examined. The results are shown in FIG. 12. As a result, a positive correlation was observed, in which the less the thiomethylation modification, the lower the insulin secretory capacity.

The foregoing merely illustrates objects and subjects of the present invention, and does not limit the accompanying Claims. Without departing from the accompanying Claims, various modifications and alterations to the described embodiments will be apparent to those skilled in the art in view of the teachings herein.

INDUSTRIAL APPLICABILITY

The use of the detection method of the present invention makes it possible to detect an RNA modification (e.g., thiomethylation) within a short period of time, at low cost, and with high sensitivity. In addition, the use of the detection method of the present invention makes it possible to detect an RNA modification (e.g., thiomethylation of tRNA) using a small amount of RNA sample (e.g., tRNA from peripheral blood) to diagnose the onset risk of a disease (e.g., diabetes).

The invention claimed is:

1. A method for detecting an RNA modification present in RNA in a sample, comprising:
(a) a step of producing cDNA by reverse transcription of the RNA using a first primer, the first primer being an oligonucleotide designed to complementarily bind to a region including a site having the RNA modification on the RNA;
(b) a step of producing cDNA by reverse transcription of the RNA using a second primer, the second primer being an oligonucleotide designed to complementarily bind to a region 3' of the site having the RNA modification on the RNA, wherein the step (a) and (b) are performed separately or simultaneously, and measuring the difference between the amounts of cDNA produced in the respective steps, thereby detecting the RNA modification.

2. The method according to claim 1, wherein the steps (a) and (b) are performed separately.

3. The method according to claim 2, wherein the difference between the amounts of cDNA is measured by a nucleic acid amplification reaction method or a fluorescence method.

4. The method according to claim 3, wherein the nucleic acid amplification reaction method is a quantitative PCR method or a real-time quantitative PCR method.

5. The method according to claim 4, wherein the difference between the amounts of cDNA is measured as a difference in the rate at which a PCR product of the cDNA accumulates in the nucleic add amplification reaction method.

6. The method according to claim 1, wherein the RNA modification present in RNA is thiomethylation, methylation, or tauination present in tRNA.

7. The method according to claim 6, wherein the thiomethylation present in tRNA is the thiomethylation of adenosine$^{37}$ in tRNA corresponding to Lys, tRNA corresponding to Trp, tRNA corresponding Phe, or tRNA corresponding to Ser (UCN).

8. The method according to claim 7, wherein the thiomethylation present in tRNA is the thiomethylation of adenosine$^{37}$ in tRNA corresponding to Lys.

9. The method according to claim 8, wherein the RNA contains RNA derived from human peripheral blood.

10. A method for diagnosis of a type 2 diabetes or the risk thereof comprising the use of the method according to claim 8, wherein the RNA is the tRNA derived from a subject and the absence or a decrease of the thiomethylation of adenosine$^{37}$ in tRNA corresponding to Lys is indicative of a type 2 diabetes or the risk thereof in the subject.

11. The method according to claim 10, wherein the tRNA is derived from the subject's tissue or blood.

12. The method according to claim 10, further comprising assaying the insulin secretory capacity of the subject.

13. The method according to claim 12, wherein the tRNA is derived from the subject's tissue or blood.

14. The method according to claim 1, wherein the sample includes at least two samples having known rates of RNA modification present in RNA and a sample having an unknown RNA modification rate, and further comprising performing the steps (a) and (b) for each sample and comparing a parameter indicating a difference in cDNA amount measured from each sample with one another, thereby measuring the unknown RNA modification rate.

15. The method according to claim 14, wherein the difference between the amounts of cDNA is measured by a nucleic acid amplification reaction method, wherein the nucleic acid amplification reaction method is a quantitative PCR method or a realtime quantitative PCR method, and wherein the parameter is a difference in threshold cycle for amplifying cDNA derived from the first primer and the second primer.

16. The method according to claim 1, wherein the sample has an unknown RNA modification rate, and further comprising comparing a parameter indicating a difference in cDNA amount measured from the sample with a predetermined calibration curve, thereby measuring the unknown RNA modification rate.

17. The method according to claim 16, wherein the difference between the amounts of cDNA is measured by a nucleic acid amplification reaction method, wherein the nucleic acid amplification reaction method is a quantitative PCR method or a realtime quantitative PCR method, and wherein the parameter is a difference in threshold cycle for amplifying cDNA derived from the first primer and the second primer.

18. A kit for detecting an RNA modification present in tRNA in an sample, the kit including:
  a first primer that is an oligonucleotide designed to complementarily bind to a region including a site having the RNA modification on the tRNA; and a second primer that is an oligonucleotide designed to complementarily bind to a region 3' of the site having the RNA modification on the tRNA, wherein at least one of the first and second primer is labeled.

19. The kit according to claim 18, wherein the RNA modification present in tRNA is thiomethylation, methylation, or taurination.

20. The kit according to claim 19, wherein the thiomethylation present in tRNA is the thiomethylation of adenosine$^{37}$ in tRNA corresponding to Lys, tRNA corresponding to Trp, tRNA corresponding to Phe, or tRNA corresponding to Ser (UCN).

* * * * *